US008293708B2

(12) United States Patent
Reslow

(10) Patent No.: US 8,293,708 B2
(45) Date of Patent: Oct. 23, 2012

(54) LIQUID FORMULATIONS N-TERMINAL SERINE OF PEGYLATED GROWTH HORMONE

(75) Inventor: Mats Reslow, Lund (SE)

(73) Assignee: Novo Nordisk Health Care A/G, Zurich (CH)

( * ) Notice: Subject to any disclaimer, the term of this patent is extended or adjusted under 35 U.S.C. 154(b) by 503 days.

(21) Appl. No.: 12/063,278

(22) PCT Filed: Aug. 30, 2006

(86) PCT No.: PCT/EP2006/065819
§ 371 (c)(1),
(2), (4) Date: Jan. 30, 2009

(87) PCT Pub. No.: WO2007/025988
PCT Pub. Date: Mar. 8, 2007

(65) Prior Publication Data
US 2009/0325865 A1   Dec. 31, 2009

(30) Foreign Application Priority Data
Aug. 30, 2005   (EP) ..................... 05107917

(51) Int. Cl.
*A61K 38/27* (2006.01)
*C07K 14/61* (2006.01)
*A61K 38/00* (2006.01)
*C07K 1/107* (2006.01)

(52) U.S. Cl. ....... 514/11.3; 514/11.4; 514/3.2; 514/640; 424/198.1; 530/350; 530/399; 530/402

(58) Field of Classification Search .................. None
See application file for complete search history.

(56) References Cited

U.S. PATENT DOCUMENTS

| | | | |
|---|---|---|---|
| 4,179,337 A | 12/1979 | Davis et al. | |
| 5,795,560 A | 8/1998 | Reed | |
| 5,981,718 A | 11/1999 | Olsen et al. | |
| 6,010,871 A | 1/2000 | Takahara et al. | |
| 6,077,939 A | 6/2000 | Wei et al. | |
| 6,566,506 B2 | 5/2003 | Greenwald et al. | |
| 6,673,347 B1 | 1/2004 | Offord et al. | |
| 7,056,942 B2 | 6/2006 | Hildesheim et al. | |
| 7,524,813 B2 | 4/2009 | Zundel et al. | |
| 7,816,320 B2* | 10/2010 | Hays et al. | 514/11.4 |
| 2003/0190304 A1 | 10/2003 | Thompson et al. | |
| 2004/0127417 A1 | 7/2004 | Finn | |
| 2005/0170404 A1* | 8/2005 | Cho et al. | 435/6 |
| 2006/0135427 A1 | 6/2006 | Hays et al. | |
| 2007/0099917 A1 | 5/2007 | Nice et al. | |
| 2007/0105770 A1 | 5/2007 | Johansen et al. | |
| 2007/0111926 A1 | 5/2007 | Zundel et al. | |
| 2009/0325865 A1 | 12/2009 | Reslow | |

FOREIGN PATENT DOCUMENTS

| | | |
|---|---|---|
| CN | 1528787 A | 9/2004 |
| EP | 243929 A2 | 11/1987 |
| EP | 605963 A2 | 7/1994 |
| EP | 785276 A1 | 7/1997 |
| EP | 950665 A1 | 10/1999 |
| EP | 1548016 A1 | 6/2005 |
| JP | 2008-525494 | 7/2008 |
| RU | 2385879 | 2/2008 |
| WO | 90/03401 A1 | 4/1990 |
| WO | WO/93/12812 * | 7/1993 |
| WO | 95/32003 A1 | 11/1995 |
| WO | 96/41813 A2 | 12/1996 |
| WO | WO/96/41813 * | 12/1996 |
| WO | WO 96/41813 A2 | 12/1996 |
| WO | WO 96/41813 A3 | 12/1996 |
| WO | 97/39768 A1 | 10/1997 |
| WO | WO 97/39768 | 10/1997 |
| WO | 98/05363 | 2/1998 |
| WO | WO 98/05363 | 2/1998 |
| WO | 98/26747 A2 | 6/1998 |
| WO | 01/70685 A2 | 9/2001 |
| WO | WO-02/055532 | 7/2002 |
| WO | 03/044056 A2 | 5/2003 |
| WO | 2004/000366 A1 | 12/2003 |
| WO | 2004/007687 A2 | 1/2004 |
| WO | 2004/108667 A2 | 12/2004 |
| WO | 2005/014024 A2 | 2/2005 |
| WO | WO 2005/014024 A2 | 2/2005 |
| WO | WO 2005/014024 A3 | 2/2005 |
| WO | 2005/034988 A1 | 4/2005 |
| WO | 2005/035553 A2 | 4/2005 |
| WO | 2005/035565 A1 | 4/2005 |
| WO | 2005/070468 A2 | 8/2005 |
| WO | 2005/074546 A2 | 8/2005 |
| WO | WO 2005/074546 A2 | 8/2005 |
| WO | WO 2005/074546 A3 | 8/2005 |
| WO | WO 2005/074650 | 8/2005 |
| WO | WO2005074546 * | 8/2005 |
| WO | 2006/042848 A2 | 4/2006 |
| WO | 2006042847 A2 | 4/2006 |
| WO | WO 2006/042848 A2 | 4/2006 |
| WO | WO 2006/042848 A3 | 4/2006 |
| WO | 2006/069220 A2 | 6/2006 |
| WO | WO 2006/069220 A2 | 6/2006 |
| WO | 2006/134148 A2 | 12/2006 |
| WO | 2007/025988 A2 | 3/2007 |

OTHER PUBLICATIONS

Rose K et al: Natural Peptides as Building Blocks for the Synthesis of Large Protein-like Molecules with Hydrazone and Oxime Linkages. Bioconjugate Chemistry, 7, 552-556, 1996.*

Clark, R. et al., "Long-acting Growth Hormones Produced by Conjugation with Polyethylene Glycol", The Journal of Biological Chemistry, 1996, vol. 271, No. 36, pp. 21969-21977.

Shao, J. et al., "Unprotected Peptides as Building Blocks for the Synthesis of Peptide Dendrimers with Oxime, Hydrazone, and Thiazolidine Linkages", Journal of the American Chemical Society, 1995, vol. 117, No. 14, pp. 3893-3899.

(Continued)

*Primary Examiner* — Elly-Gerald Stoica
(74) *Attorney, Agent, or Firm* — Teresa Chen

(57) ABSTRACT

Pharmaceutical compositions comprising pegylated growth hormone at pH 7 or below are provided.

4 Claims, 1 Drawing Sheet

OTHER PUBLICATIONS

Rose, K. et al., "Natural Peptides as Building Blocks for the Synthesis of Large Protein-Like Molecules with Hydrazone and Oxime Linkages", Bioconjugate Chemistry, 1996, vol. 7, pp. 552-556.

Breinbauer, R et al. Chembiochem Azide—Alkyne Coupling: A Powerful Reaction for . . . 2003 4 11 1147-1149.

Baumann G et al. Metabolism: Clinical and Experimental In-Vivo Kinetics of a Covalent Growth Hormone-Binding Protein Complex 1989 38 4 330-333.

Durieux, P. et al. Tetrahedron Letters. Synthesis of Biotinylated Glycosulfopeptides by . . . 2001 42 12 2297-2299.

Gorman, J.J et al. The Journal of Biological Chemistry Transglutaminase Amine Substrates for Photothermal Labeling and Cleavable Cross-Linking of Proteins 1980 255 3 1175-1180.

Gaertner, H.F. et al Bioconjugate Chemistry Site-Specific Attachment of Functionalized . . . 1996 7 1 38-44.

Huntsman—HTTP://HUNTMAN.COM/TEXTILE_EFFECTS/MEDIA/CIBACRON_RAC_BROCHURE.PDF 2008—4 pages.

Ingallinella, P. et al. Bioorganic & Medicinal Chemistry Letters A New Method for Chemoselective Conjugation of . . . 2001 11 10 1343-1346.

King, H.D et al. Bioconjugate Chemistry Monoclonal Antibody Conjugates of . . . 1999 10 2 279-288.

Sato, H Advanced Drug Delivery Reviews Enzymatic Procedure for Site-Specific Pegylation of Proteins 2002 54—487-504.

Sato, H et al. Bioconjugate Chemistry Transglutaminase-Mediated Dual and Site-Specific Incorporation of Poly . . . 2000 11 4 502-509.

Scott, W.L et al. Bioorganic & Medicinal Chemistry Letters Synthesis of Reagents for the One Step Incorporation of Hydrazide Functionality Onto the Lysine Residues . . . 1996 6 13 1491-1496.

Stella Journal of Pharmaceutical Sciences Prodrugs: Some Thoughts and Current Issues 2010 99—4755-4765.

Thumshirn, G et al. European Journal of Medicinal Chemistry. Multimeric Cyclic RGD Peptides as Potential Tools for . . . 2003 9 12 2717-2725.

Shao et al., Journal of the American Chemical Society—1995 117—3893-3899.

Vippagunta et al. Advanced Drug Delivery Reviews Crystalline Solids 2001 48—3-26.

Wada, E et al. Biotechnology Letters Enzymatic Modification of . . . 2001 23—1367-1372.

Wilkinson, Ian R. et al. Nature Medicine a Ligand-Receptor Fusion of Growth Hormone Forms a Dimer and ISA Potent Long-Acting Agonist 2007 13 9 1108-1113.

Yurkovetskiy, A. et al. Biomacromolecules. Fully Degradable Hydrophilic Polyals for Protein Modification 2005 6 5 2648-2658.

Zhang, L et al. Proceedings of the National Academy of Sciences of the USA Preparation of Functionally Active Cell-Permeable Peptides by 1998 95 16 9184-9189.

Zalipsky S Bioconjugate Chemistry Functionalized Poly Ethylene Glycol for Preparation of Biologically Relevant Conjugates 1995 6 2 150-165.

Zatsepin et al. Bioconjugate Chemistry—2002 13—822-830.

Zhang and Tam Analytical Biochemistry—1996 233—87-93.

U.S. Appl. No. 60/957,732, filed Aug. 24, 2007, Buchardt.

Dictionary Definition of Composition Retrieved From http://www.merriam-webster.com.dictionary/composition on Apr. 19, 2011, 3 pages.

Reactive Dye Affinity Chromatography Matrices, Sigma Website, http://sigmaaldrich.com, Oct. 30, 1996, pp. 1-4.

* cited by examiner

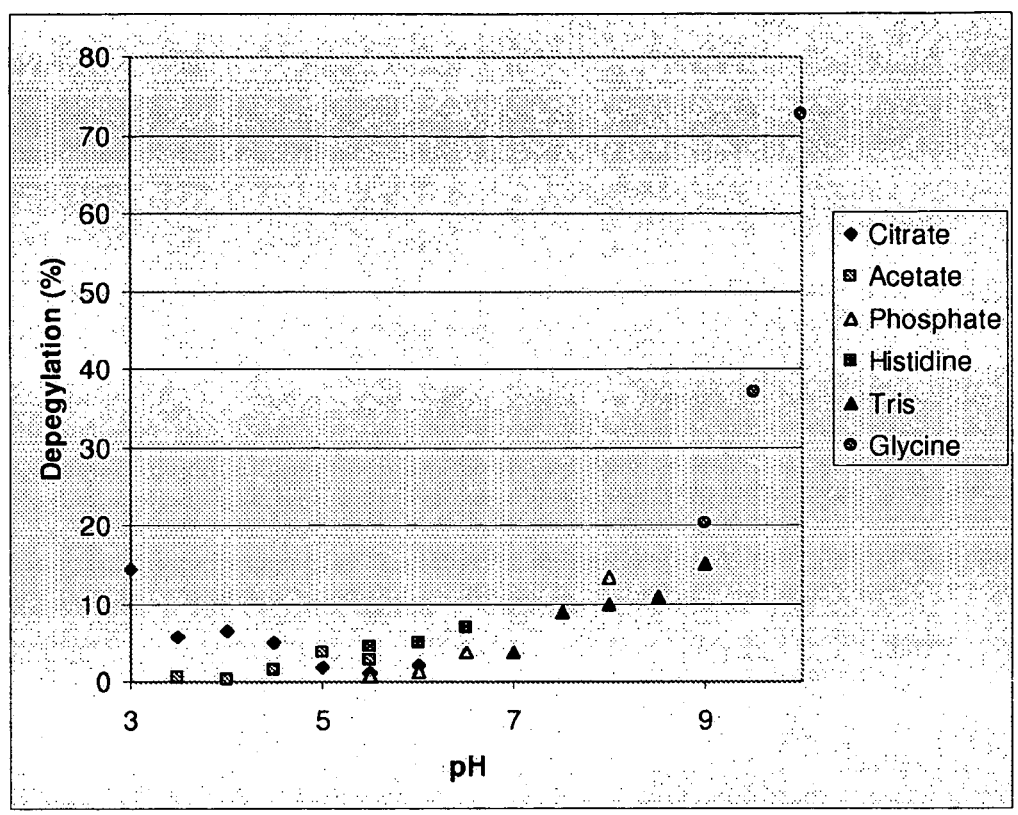

LIQUID FORMULATIONS N-TERMINAL SERINE OF PEGYLATED GROWTH HORMONE

CROSS-REFERENCE TO RELATED APPLICATIONS

This application is a 35 U.S.C. §371 national stage application of International Patent Application PCT/EP2006/065819 (published as WO 2007/025988 A2), filed Aug. 30, 2006, which claimed priority of European Patent Application 05107917.6, filed Aug. 30, 2005; this application further claims priority under 35 U.S.C. §119 of U.S. Provisional Application 60/713,283, filed Sep. 1, 2005 and U.S. Provisional Application 60/718,499, filed Sep. 19, 2005.

FIELD OF THE INVENTION

The invention relates to pharmaceutical compositions comprising pegylated growth hormone wherein the PEG is attached to the growth hormone via an oxime bond. The stabilised compositions are useful in therapy.

BACKGROUND OF THE INVENTION

The growth hormone from man and from the common domestic animals are proteins of approximately 191 amino acids, synthesized and secreted from the anterior lope of the pituitary gland. Human growth hormone consists of 191 amino acids with the sequence FPTIPLSRLFDNAML-RAHRLHQLAFDTYQEFEEAYIPKEQKYS-FLQNPQTSLCFSESIPTPSN REETQQKSNLELLRIS-LLLIQSWLEPVQFLRSVFANSLVYGASDSNVYDLLKD LEEGIQTLMG RLEDGSPRTGQIFKQTYSKFDTN-SHNDDALLKNYGLLYCFRKDMDKVETFL-RIVQCRSVEG SCGF, SEQ ID No. 1.

Growth hormone is a key hormone involved in the regulation of not only somatic growth, but also in the regulation of metabolism of proteins, carbohydrates and lipids. The major effect of growth hormone is to promote growth. The organ systems affected by growth hormone include the skeleton, connective tissue, muscles, and viscera such as liver, intestine, and kidneys.

The metabolic effect of growth hormones is mediated by Insulin-like Growth Factor-I (IGF-I). IGF-I is primarily produced in the liver and it circulates in the plasma bound to specific binding proteins, the most important of which is Insulin-like Protein Binding Protein-3 (IGFBP-3). Growth hormone appears to exert its activity through two distinct mechanisms. In the post-prandial period, the effect is mediated through IGF-1 and result is glucose uptake, lipogenesis and proteinogenesis. When fasting, i.e. when the blood glucose is low, the growth hormone secretion is boosted, where it increases lipoxidation. It is thus noteworthy that growth hormone both in the post-prandial period and in fasting periods acts to preserve and build up proteins.

Growth hormone is used to treat growth hormone deficiency, e.g. various forms of short stature. Unfortunately, growth hormone has a relative short half life which means that patients receiving growth hormone treatment typically need daily growth hormone administration. Growth hormone being a protein, the administration form is injections which represents a daily inconvenience to the patients.

In an attempt to lower the administration frequency, growth hormone in a sustained release formulation has been marketed under the trade name Nutropin Depot®. Another approach to lower the administration frequency is to manipulate the growth hormone molecule to increase the half life. Well-known ways to increase half life of proteins include PEGylation (U.S. Pat. No. 4,179,337 and J. Biol. Chem. 271, 21969-21977 (1996)), which probably works by increasing the molecular size of the molecule to decrease renal clearance and by making the molecule less susceptible to protease break down.

The PEG moiety may be attached to PEG via different forms of bonds or linkages including amide bonds obtained by acylation of free amino groups. Alternatively, a functional group may be introduced into growth hormone, which group is reacted with a functionalised PEG moiety in a subsequent step. This approach often has the advantage of improved selectivity as the introduced functional group may be selected so that it is unique to growth hormone. U.S. Pat. No. 6,673,347 discloses that polymeric groups may be attached to proteins by means of an oxime bond. An oxime bond may be formed in a reaction between a carbonyl functionalised, such as an aldehyde functionalised growth hormone and an amineoxy functionalised PEG, or vice verse in a reaction between an amineoxy functionalised growth hormone and a carbonyl, such as an aldehyde functionalised PEG.

WO 97/39768 discloses that human growth hormone may be formulated at pH between 6.0 and 8.8.

J. Am. Chem. Soc. 117, 3893-3899 (1995) discloses that the rate of oxime bond formation has its maximum at pH fairly low pH, i.e. around or below 5.7.

The present invention aims at providing pharmaceutical compositions for pegylated growth hormone wherein the PEG is attached to the growth hormone via an oxime bond. Such formulations have improved or alternative properties compared to known formulations.

SUMMARY OF THE INVENTION

The present inventor have surprisingly found that compositions comprising pegylated growth hormone wherein the PEG moiety is attached to the growth hormone via an oxime bond is markedly more stable at neutrale or acid pH. Accordingly, in one embodiment, the invention relates to a pharmaceutical compositions comprising a pegylated growth hormone, wherein said pegylated growth hormone comprises growth hormone and a PEG moiety, wherein said growth hormone and said PEG moiety is connected via an oxime bond, and optionally via a linker, said formulation having a pH of 7 or below.

In one embodiment, the invention relates to a method of treating diseases benefiting from an increase in the plasma level of growth hormone, the method comprising administering to a patient in need thereof an therapeutically effective amount of a composition of the present invention.

In one embodiment, the invention relates to the use of a composition of the present invention in the manufacture of a medicament for the treatment of a disease which will benefit from an increase in the plasma level of growth hormone.

DESCRIPTION OF THE DRAWINGS

FIG. 1 shows the amount of depegylated growth hormone formed as a function of pH in different 20 mM buffers. The data are from the experiment as described in example 7.

DESCRIPTION OF THE INVENTION

The present invention relates to a pharmaceutical composition comprising a pegylated growth hormone, wherein said pegylated growth hormone comprises growth hormone and a PEG, wherein said growth hormone and said PEG is connected via an oxime bond, and optionally via a linker, said formulation having a pH of 7 or below.

The term "PEG" is intended to indicate polyethylene glycol of a molecular weight between approximately 100 and approximately 1,000,000 Da, including analogues thereof, wherein for instance the terminal OH-group has been replaced by an alkoxy group, such as a methoxy group, an ethoxy group or a propoxy group. In particular, the PEG wherein the terminal OH group has been replaced by methoxy is referred to as mPEG.

The term "mPEG" (or more properly "mPEGyl") means a polydisperse or monodisperse radical of the structure

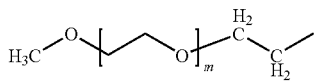

wherein m is an integer larger than 1. Thus, a mPEG wherein m is 90 has a molecular weight around 4000 Da, i.e. approx 4 kDa. Likewise, a mPEG with an average molecular weight of 20 kDa has an average m of 453. Due to the process for producing mPEG these molecules often have a distribution of molecular weights. This distribution is described by the polydispersity index.

The term "polydispersity index" as used herein means the ratio between the weight average molecular weight and the number average molecular weight, as known in the art of polymer chemistry (see e.g. "Polymer Synthesis and Characterization", J. A. Nairn, University of Utah, 2003). The polydispersity index is a number which is greater than or equal to one, and it may be estimated from Gel Permeation Chromatographic data. When the polydispersity index is 1, the product is monodisperse and is thus made up of compounds with a single molecular weight. When the polydispersity index is greater than 1 it is a measure of the polydispersity of that polymer, i.e. how broad the distribution of polymers with different molecular weights is.

The use of for example "mPEG20000" or "mPEG(20 k)" in formulas, compound names or in molecular structures indicates an mPEG residue wherein mPEG is polydisperse and has a molecular weight of approximately 20 kDa.

The polydispersity index typically increases with the molecular weight of the PEG or mPEG. When reference is made to 20 kDa PEG and in particular 20 kDa mPEG it is intended to indicate a compound (or in fact a mixture of compounds) with a polydisperisty index below 1.06, such as below 1.05, such as below 1.04, such as below 1.03, such as between 1.02 and 1.03. When reference is made to 30 kDa PEG and in particular 30 kDa mPEG it is intended to indicate a compound (or in fact a mixture of compounds) with a polydisperisty index below 1.06, such as below 1.05, such as below 1.04, such as below 1.03, such as between 1.02 and 1.03. When reference is made to 40 kDa PEG and in particular 40 kDa mPEG it is intended to indicate a compound (or in fact a mixture of compounds) with a polydisperisty index below 1.06, such as below 1.05, such as below 1.04, such as below 1.03, such as between 1.02 and 1.03.

The term "pegylated GH" or "pegylated hGH" is intended to indicate GH or hGH which has been covalently attached to PEG, i.e. it indicates a conjugate comprising GH or hGH and PEG, wherein said GH or hGH and said PEG are covalently attached, and in the present context via an oxime bind. Said attachment may further be via a linker.

The term "conjugate" as a noun is intended to indicate a modified peptide, i.e. a peptide with a moiety bonded to it to modify the properties of said peptide. As a verb, the term is intended to indicate the process of bonding a moiety to a peptide to modify the properties of said peptide.

The following is a non-limiting list of embodiments, which is further described elsewehere herein.

Embodiment 1: A pharmaceutical composition comprising a pegylated growth hormone, wherein said pegylated growth hormone comprises growth hormone and a PEG, wherein said growth hormone and said PEG is connected via an oxime bond, and optionally via a linker, said formulation having a pH of 7 or below.

Embodiment 2: The composition according to embodiment 1, wherein said formulation does not comprise any substantial amount of carbonate.

Embodiment 3: The composition according to embodiment 1 or embodiment 2, wherein said pegylated growth hormone is present in a concentration from 0.001 to 100 mg/ml.

Embodiment 4: The composition according to embodiment 3, wherein said pegylated growth hormone is present in a concentration from 0.01 to 100 mg/ml.

Embodiment 5: The composition according to embodiment 4, wherein said pegylated growth hormone is present in a concentration from 1 to 100 mg/ml.

Embodiment 6: The composition according to embodiment 5, wherein said pegylated growth hormone is present in a concentration from 5 to 50 mg/ml.

Embodiment 7: The composition according to embodiment 6, wherein said pegylated growth hormone is present in a concentration from 30 to 50 mg/ml.

Embodiment 8: The composition according to embodiment 7, wherein said pegylated growth hormone is present in a concentration of about 40 mg/ml.

Embodiment 9: The composition according any of embodiments 1 to 8, which further comprises histidine in a concentration of from 0.001 to 10 mg histidine per mg of growth hormone.

Embodiment 10: The composition according embodiment 9, which comprises histidine in a concentration of from 0.01 to 1 mg histidine per mg of growth hormone.

Embodiment 11: The composition according embodiment 10, which comprises histidine in a concentration of from 0.02 to 0.05 mg histidine per mg of growth hormone.

Embodiment 12: The composition according any of embodiments 1 to 8, which further comprises histidine in a concentration of from 0.002 to 0.35 mg per mg of pegylated growth hormone.

Embodiment 13: The composition according embodiment 12, which comprises histidine in a concentration of from 0.003 to 0.035 mg histidine per mg of pegylated growth hormone.

Embodiment 14: The composition according embodiment 13, which comprises histidine in a concentration of from 0.01 to 0.02 mg histidine per mg of pegylated growth hormone.

Embodiment 15: The composition according to any of embodiments 1 to 14, which further comprises histidine in a concentration from 0.05 to 100 mg/ml.

Embodiment 16: The composition according to embodiment 15, which comprises histidine in a concentration from 0.05 to 1 mg/ml.

Embodiment 17: The composition according to embodiment 16, which comprises histidine in a concentration from 0.1 to 0.5 mg/ml.

Embodiment 18: The composition according to any of embodiments 1 to 17, which further comprises glycine in a concentration from 1 to 20 mg/ml.

Embodiment 19: The composition according to embodiment 18, which comprises glycine in a concentration from 2 to 10 mg/ml.

Embodiment 20: The composition according to any of embodiments 1 to 19 which further comprises a non-ionic surfactant at a concentration from 1 to 10 mg/ml.

Embodiment 21: The composition according to embodiment 20, wherein said non-ionic surfactant is poloxamer 188.

Embodiment 22: The composition according to any of embodiments 1 to 21, which further comprises a sugar alcohol at a concentration from 5 to 10 mg/ml.

Embodiment 23: The composition according to any of embodiments 1 to 21, which further comprises a sugar alcohol at a concentration from 5 to 100 mg/ml.

Embodiment 24: The composition according to embodiment 23, which comprises said sugar alcohol in a concentration from 15 to 50 mg/ml.

Embodiment 25: The composition according to embodiment 24, which comprises said sugar alcohol in a concentration of about 20 mg/ml.

Embodiment 26: The composition according to any of embodiments 23 to 25, wherein said sugar alcohol is mannitol.

Embodiment 27: The composition according to any of embodiments 1 to 26, which further comprises a phosphate buffer at a final phosphate concentration from 5 to 50 mM.

Embodiment 28: The composition according to any of embodiments 1 to 26, which further comprises a phosphate buffer at a final phosphate concentration from 0.1 to 5 mM.

Embodiment 29: The composition according to embodiment 28, which comprises a phosphate buffer at a final phosphate concentration of 4.5 mM.

Embodiment 30: The composition according to any of embodiments 1 to 26, which further comprises a citrate buffer at a buffer concentration from 5 to 50 mM.

Embodiment 31: The composition according to any of embodiments 1 to 26, which further comprises a citrate buffer at a buffer concentration from 0.1 to 5 mM.

Embodiment 32: The composition according to any of embodiments 1 to 26, which further comprises an acetate buffer at a buffer concentration from 5 to 50 mM.

Embodiment 33: The composition according to any of embodiments 1 to 26, which further comprises an acetate buffer at a buffer concentration from 0.1 to 5 mM.

Embodiment 34: The composition according to any of embodiments 1 to 33, which further comprises a preservative selected from phenol, m-cresol and/or benzylalcohol at a concentration from 1 to 10 mg/ml.

Embodiment 35: The composition according to embodiment 34, wherein said preservative is present in a concentration from 1 to 5 mg/ml.

Embodiment 36: The composition according to embodiment 34 or embodiment 35, wherein said preservative is phenol.

Embodiment 37: The composition according to any of embodiments 1 to 36 comprising

| | |
|---|---|
| Histidine: | 0.1 to 1.0 mg per mg of pegylated growth hormone |
| Poloxamer 188: | 2 to 4 mg/ml |
| Mannitol: | 30 to 50 mg/ml |
| Phenol: | 1 to 5 mg/ml |
| pegylated growth hormone: | 0.1 to 5.0 mg/ml |
| pH: | 5-7 |

Embodiment 38: The composition according to embodiment 37 comprising

| | |
|---|---|
| Histidine: | 0.54 mg per mg of pegylated growth hormone |
| Poloxamer 188: | 3 mg/ml |
| Mannitol: | 40 mg/ml |
| Phenol: | 2.5 mg/ml |
| pegylated growth hormone: | 0.1-5.0 mg/ml |
| pH: | 6.1. |

Embodiment 39: The composition according to any of embodiments 1 to 36 comprising

| | |
|---|---|
| Glycin: | 3 to 7 mg/ml |
| Mannitol: | 10 to 30 mg/ml |
| Total $PO_4^{3-}$: | 5 to 20 mM |
| Phenol: | 1 to 5 mg/ml |
| pegylated growth hormone: | 0.1 to 5 mg/ml |
| pH: | 5-7. |

Embodiment 40: The composition according to embodiment 39 comprising

| | |
|---|---|
| Glycin: | 4.4 mg/ml |
| Mannitol: | 22 mg/ml |
| Total $PO_4^{3-}$: | 9 mM |
| Phenol: | 2.5 mg/ml |
| pegylated growth hormone: | 0.1-5 mg/ml |
| pH: | 6.1-7.3 |

Embodiment 41: The composition according to any of embodiments 1 to 36 comprising

| | |
|---|---|
| Histidine: | 0.002 to 0.34 mg per mg of pegylated growth hormone |
| Poloxamer 188: | 1 to 4 mg/ml |
| Mannitol: | 10 to 30 mg/ml |
| Phenol: | 1 to 5 mg/ml |
| pegylated growth hormone: | 1 to 200 mg/ml |
| pH: | 5-7. |

Embodiment 42: The composition according to embodiment 41 comprising

| | |
|---|---|
| Histidine: | 0.0085 mg per mg of pegylated growth hormone |
| Poloxamer 188: | 1.5 mg/ml |
| Mannitol: | 20 mg/ml |
| Phenol: | 5 mg/ml |
| pegylated growth hormone: | 1 to 200 mg/ml |
| pH: | 6.1. |

Embodiment 43: The composition according to any of embodiments 1 to 36 comprising

| | |
|---|---|
| Glycin: | 2 to 7 mg/ml |
| Mannitol: | 10 to 30 mg/ml |
| Total $PO_4^{3-}$: | 2 to 20 mM |
| Phenol: | 1 to 5 mg/ml |
| pegylated growth hormone: | 1 to 200 mg/ml |
| pH: | 5-7 |

Embodiment 44: The composition according to embodiment 43 comprising

| | |
|---|---|
| Glycin: | 2.2 mg/ml |
| Mannitol: | 11 mg/ml |
| Total $PO_4^{3-}$: | 4.5 mM |
| Phenol: | 5 mg/ml |
| pegylated growth hormone: | 1 to 200 mg/ml |
| pH: | 5-7 |

Embodiment 45: The composition according to any of embodiments 1 to 44, wherein said pegylated growth hormone comprises human growth hormone.

Embodiment 46: The composition according to any of embodiments 1 to 45, wherein the PEG moiety is attached to the growth hormone in the N-terminal of said growth hormone.

Embodiment 47: The composition according to any of embodiments 1 to 46, wherein said pegylated growth hormone is selected from Lys$^\epsilon$(4-((2-(1-(mPEGcarbonyl)piperidin-4-yl)ethoxy)imino)pentanoyl) 192)hGH(1-192) amide, in which mPEG has a molecular weight of 20 kDa, (S)-2-(hGHylamino)-6-(4-((2-(1-(4-(mPEGyloxy)butanoyl)piperidin-4-yl)ethoxy)imino)-pentanoylamino)hexanoic amide, in which mPEG has a molecular weight of 10 kDa, $N^{\epsilon 141}$-[2-(4-(4-(mPEG(20 k)ylbutanoyl)-amino-butyloxy-imino)-ethyl]hGH, $N^{\epsilon 141}$-[2-(1-(hexadecanoyl)piperidin-4-yl)ethyloxyimino)-ethyl]hGH, $N^{\epsilon 141}$ (2-(4-(4-(1,3-bis(mPEG(20 k)ylaminocarbonyloxy)prop-2-yloxy)butyrylamino)-butyloxyimino)ethyl)hGH, $N^{\epsilon 141}$ (2-(4-(2,6-bis(mPEG(20 k)yloxycarbonylamino)hexanoylamino)butyloxyimino)ethyl)hGH, $N^{\epsilon 141}$ (2-(4-(4-(mPEG(30 k)yloxy)butyrylamino)butyloxyimino)ethyl)hGH, $N^{\epsilon 141}$ (2-(4-(4-(mPEG(20 k)yloxy)butyrylamino)butyloxyimino)ethyl)hGH, and $N^{\epsilon 141}$ (2-(4-(3-(mPEG(30 k)yloxy)propanoylamino)butyloxyimino)ethyl)hGH, wherein mPEG(20 k)yl and mPEG(30 k)yl is intended to indicate mPEG(20 k)yl and mPEG(30 k)yl, respectively, with a polydispersity index below 1.06, or

[MeO—(CH$_2$CH$_2$O)$_{400-500}$—CH$_2$CH$_2$—NH—C(=O)—O—CH$_2$]$_2$CH—O—(CH$_2$)$_3$—C(=O)—NH—(CH$_2$)$_4$—O—N=CH—C(=O)-GH,

[MeO—(CH$_2$CH$_2$O)$_{600-750}$](CH$_2$)$_3$—C(=O)NH—(CH$_2$)$_4$CH[MeO—(CH$_2$CH$_2$O)$_{600-750}$—(CH$_2$)$_3$C(=O)NH]—C(=O)NH—(CH$_2$)$_4$—O—N=CH—C(=O)-GH,

MeO—(CH$_2$CH$_2$O)$_{400-500}$—CH$_2$CH$_2$CH$_2$—C(=O)—NH—(CH$_2$)$_4$—O—N=CH—C(=O)-GH,

MeO—(CH$_2$CH$_2$O)$_{600-700}$—CH$_2$CH$_2$CH$_2$—C(=O)—NH—(CH$_2$)$_4$—O—N=CH—C(=O)-GH,

MeO—(CH$_2$CH$_2$O)$_{850-950}$—CH$_2$CH$_2$CH$_2$—C(=O)—NH—(CH$_2$)$_4$—O—N=CH—C(=O)-GH,

[MeO—(CH$_2$CH$_2$O)$_{400-500}$]—C(=O)NH—(CH$_2$)$_4$—CH[MeO—(CH$_2$CH$_2$O)$_{400-500}$—C(=O)NH]—C(=O)NH—(CH$_2$)$_4$—O—N=CH—C(=O)-GH,

[MeO—(CH$_2$CH$_2$O)$_{600-700}$]—C(=O)NH—(CH$_2$)$_4$—CH[MeO—(CH$_2$CH$_2$O)$_{600-700}$—C(=O)NH]—C(=O)NH—(CH$_2$)$_4$—O—N=CH—C(=O)-GH,

MeO—(CH$_2$CH$_2$O)$_{400-500}$—CH$_2$CH$_2$CH$_2$—C(=O)—NH—(CH$_2$)$_4$—O—N=CH—CH$_2$—O—(CH$_2$)$_4$-GH,

MeO—(CH$_2$CH$_2$O)$_{600-700}$—CH$_2$CH$_2$CH$_2$—C(=O)—NH—(CH$_2$)$_4$—O—N=CH—CH$_2$—O—(CH$_2$)$_4$-GH,

MeO—(CH$_2$CH$_2$O)$_{850-950}$—CH$_2$CH$_2$CH$_2$—C(=O)—NH—(CH$_2$)$_4$—O—N=CH—CH$_2$—O—(CH$_2$)$_4$-GH,

[MeO—(CH$_2$CH$_2$O)$_{400-500}$]—C(=O)NH—(CH$_2$)$_4$—CH[MeO—(CH$_2$CH$_2$O)$_{400-500}$—C(=O)NH]—C(=O)NH—(CH$_2$)$_4$—O—N=CH—CH$_2$—O—(CH$_2$)$_4$-GH,

MeO—(CH$_2$CH$_2$O)$_{400-500}$—CH$_2$CH$_2$CH$_2$—C(=O)—NH—(CH$_2$)$_4$—O—N=CH—CH$_2$—O—(CH$_2$)$_5$-GH,

MeO—(CH$_2$CH$_2$O)$_{600-700}$—CH$_2$CH$_2$CH$_2$—C(=O)—NH—(CH$_2$)$_4$—O—N=CH—CH$_2$—O—(CH$_2$)$_5$-GH,

MeO—(CH$_2$CH$_2$O)$_{850-950}$—CH$_2$CH$_2$CH$_2$—C(=O)—NH—(CH$_2$)$_4$—O—N=CH—CH$_2$—O—(CH$_2$)$_5$-GH,

[MeO—(CH$_2$CH$_2$O)$_{400-500}$]—C(=O)NH—(CH$_2$)$_4$—CH[MeO—(CH$_2$CH$_2$O)$_{400-500}$—C(=O)NH]—C(=O)NH—(CH$_2$)$_4$—O—N=CH—CH$_2$—O—(CH$_2$)$_5$-GH,

MeO—(CH$_2$CH$_2$O)$_{400-500}$—CH$_2$CH$_2$CH$_2$—C(=O)—NH—(CH$_2$)$_4$—O—N=CH—CH$_2$—O—(CH$_2$)$_6$-GH,

MeO—(CH$_2$CH$_2$O)$_{600-700}$—CH$_2$CH$_2$CH$_2$—C(=O)—NH—(CH$_2$)$_4$—O—N=CH—CH$_2$—O—(CH$_2$)$_6$-GH,

MeO—(CH$_2$CH$_2$O)$_{850-950}$—CH$_2$CH$_2$CH$_2$—C(=O)—NH—(CH$_2$)$_4$—O—N=CH—CH$_2$—O—(CH$_2$)$_6$-GH,

[MeO—(CH$_2$CH$_2$O)$_{400-500}$]—C(=O)NH—(CH$_2$)$_4$—CH[MeO—(CH$_2$CH$_2$O)$_{400-500}$—C(=O)NH]—C(=O)NH—(CH$_2$)$_4$—O—N=CH—CH$_2$—O—(CH$_2$)$_6$-GH,

MeO—(CH$_2$CH$_2$O)$_{400-500}$—CH$_2$CH$_2$CH$_2$—C(=O)—NH—(CH$_2$)$_4$—O—N=CH—CH$_2$—O-(1,4-C$_6$H$_4$)CH$_2$-GH,

MeO—(CH$_2$CH$_2$O)$_{600-700}$—CH$_2$CH$_2$CH$_2$—C(=O)—NH—(CH$_2$)$_4$—O—N=CH—CH$_2$—O-(1,4-C$_6$H$_4$)CH$_2$-GH,

MeO—(CH$_2$CH$_2$O)$_{850-950}$—CH$_2$CH$_2$CH$_2$—C(=O)—NH—(CH$_2$)$_4$—O—N=CH—CH$_2$—O-(1,4-C$_6$H$_4$)CH$_2$-GH,

[MeO—(CH$_2$CH$_2$O)$_{400-500}$]—C(=O)NH—(CH$_2$)$_4$—CH[MeO—(CH$_2$CH$_2$O)$_{400-500}$—C(=O)NH]—C(=O)NH—(CH$_2$)$_4$—O—N=CH—CH$_2$—O-(1,4-C$_6$H$_4$)CH$_2$-GH,

MeO—(CH$_2$CH$_2$O)$_{400-500}$—CH$_2$CH$_2$CH$_2$—C(=O)—NH—(CH$_2$)$_4$—O—N=CH—CH$_2$—O-(1,3-C$_6$H$_4$)CH$_2$-GH,

MeO—(CH$_2$CH$_2$O)$_{600-700}$—CH$_2$CH$_2$CH$_2$—C(=O)—NH—(CH$_2$)$_4$—O—N=CH—CH$_2$—O-(1,3-C$_6$H$_4$)CH$_2$-GH,

MeO—(CH$_2$CH$_2$O)$_{850-950}$—CH$_2$CH$_2$CH$_2$—C(=O)—NH—(CH$_2$)$_4$—O—N=CH—CH$_2$—O-(1,3-C$_6$H$_4$)CH$_2$-GH,

[MeO—(CH$_2$CH$_2$O)$_{400-500}$]—C(=O)NH—(CH$_2$)$_4$—CH[MeO—(CH$_2$CH$_2$O)$_{400-500}$—C(=O)NH]—C(=O)NH—(CH$_2$)$_4$—O—N=CH—CH$_2$—O-(1,3-C$_6$H$_4$)CH$_2$-GH,

[Structural formula showing mPEG-C(=O)-NH-(CH2)4-O-N=C(CH3)-C6H4-C(=O)-NH-(CH2)4-CH(NH-Leu-hGH)-C(=O)-NH2]

in which mPEG has a molecular weight around 5 kDa, 10 kDa, 15 kDa, 20 kDa, 30 kDa, 40 kDa or 60 kDa, $N^{\delta 141/140}$-2-(O-(4-{4-(mPeg(10 k)yloxy)butyryl}aminobutyl)oximino)ethyl hGH, $N^{\delta 141/40}$-2-(O-(4-{3-(mPeg(10 k)yloxy)propionyl}aminobutyl)oximino)ethyl hGH, $N^{\delta 141/40}$-2-(O-(4-{4-(2,3-bis(mPeg(10 k)yloxy)prop-1-yloxy)butyryl}aminobutyl)oximino)ethyl hGH, $N^{\delta 141/40}$-2-(O-(4-{5-(mPeg(10 k)yloxy-5-oxopentanoyl}aminobutyl)oximino)ethyl hGH, $N^{\delta 141/40}$-3-({4-(2-(2-(2-(2-(4-(1,3-bis(mPeg(10 k)ylaminocarbonyloxy)prop-2-yloxy)-butyrylamino)ethoxy)ethoxy)ethoxy)butylidene}aminoxy)prop-1-yloxy hGH, $N^{\delta 141/40}$-3-({4-(1,3-bis(mPeg(10 k)ylaminocarbonyloxy)prop-2-yloxy)butylidene}-aminoxy)-propyloxy hGH, $N^{\delta 141/40}$-3-({4-(mPeg(10 k)yloxy)butylidene}aminoxy)propyloxy hGH, $N^{\delta 141/40}$-3-({4-(2,3-bis(mPeg(10 k)yloxy)prop-1-yloxy)butylidene}aminoxy)propyloxy hGH, $N^{\delta 141/40}$-3-({3-(m Peg(10 k)yloxy)propylidene}aminoxy) propyloxy hGH, $N^{\delta 141/40}$-2-(O-(2-(3-(2,3-bis(mPeg(10 k)yloxy)propyloxy)propylamino)-2-oxoethyl)oximino)ethyl hGH, $N^{141/40}$-3-({4-(2,3-bis(mPeg(10 k)yloxy)prop-1-yloxy)propylidene}aminoxy)propyloxy hGH, $N^{\delta 141/40}$-(O-(4-{4-(1,3-bis(mPeg(20 k)ylaminocarbonyloxy)prop-2-yloxy)butyryl}aminobutyl)-oximino)ethyl hGH, $N^{\delta 141/40}$-2-(O-(4-{3-(mPeg(20 k)yloxy)propionyl}aminobutyl)oximino)ethyl hGH, $N^{\delta 141/40}$-2-(O-(4-{4-(2,3-bis(mPeg(20 k)yloxy)prop-1-yloxy)butyryl}aminobutyl)oximino)ethyl hGH, $N^{\delta 141/40}$-2-(O-(4-(5-(mPeg(20 k)yloxy-5-oxopentanoylaminobutyl)oximino)ethyl hGH, $N^{\delta 141/40}$-3-({4-(2-(2-(2-(2-(4-(1,3-bis(mPeg(20 k)ylaminocarbonyloxy)prop-2-yloxy)-butyrylamino)ethoxy)ethoxy)ethoxy)butylidene}aminoxy)prop-1-yloxy hGH, $N^{\delta 141/40}$-3 ({4-(1,3-bis(mPeg(20 k)ylaminocarbonyloxy)prop-2-yloxy)butylidene}-aminoxy)-propyloxy hGH, $N^{\delta 141/40}$-3-({4-(mPeg(20 k)yloxy)butylidene}aminoxy)propyloxy hGH, $N^{\delta 141/40}$-3-({4-(2,3-bis(mPeg(20 k)yloxy)prop-1-yloxy)butylidene}aminoxy)propyloxy hGH, $N^{\delta 141/40}$-3-({3-(mPeg(20 k)yloxy)propylidene}aminoxy)propyloxy hGH, $N^{\delta 141/40}$-2-(O-(2-(3-(2,3-bis(mPeg(20 k)yloxy)propyloxy)propylamino)-2-oxoethyl)oximino)ethyl hGH, $N^{\delta 141/40}$-3-({4-(2,3-bis(mPeg(20 k)yloxy)prop-1-yloxy)propylidene}aminoxy)propyloxy hGH, $N^{\delta 141/40}$-2-(O-(4-{4-(1,3-bis(mPeg(30 k)ylaminocarbonyloxy)prop-2-yloxy)butyryl}aminobutyl)-oximino)ethyl hGH, $N^{\delta 141/40}$-2-(O-(4-{4-(mPeg(30 k)yloxy)butyryl}aminobutyl)oximino)ethyl hGH, $N^{\delta 141/40}$-2-(O-(4-{3-(mPeg(30 k)yloxy)propionyl}aminobutyl)oximino)ethyl hGH, $N^{\delta 141/40}$-2-(O-(4-{4-(2,3-bis(mPeg(30 k)yloxy)prop-1-yloxy)butyryl}aminobutyl)oximino)ethyl hGH, $N^{\delta 141/40}$-2-(O-(4-{5-(mPeg(30 k)yloxy-5-oxopentanoyl}aminobutyl)oximino)ethyl hGH, $N^{141/40}$-3-({4-(2-(2-(2-(2-(4-(1,3-bis(mPeg(30 k)ylaminocarbonyloxy)prop-2-yloxy)-butyrylamino)ethoxy)ethoxy)ethoxy)butylidene}aminoxy)prop-1-yloxy hGH, $N^{\delta 141/40}$-3-({4-(1,3-bis(mPeg(30 k)ylaminocarbonyloxy)prop-2-yloxy)butylidene}-aminoxy)-propyloxy hGH, $N^{\delta 141/40}$-3-({4-(mPeg(30 k)yloxy)butylidene}aminoxy)propyloxy hGH, $N\delta^{141/40}$-3-({4-(2,3-bis(mPeg(30 k)yloxy)prop-1-yloxy)butylidene}aminoxy)propyloxy hGH, $N^{\delta 141/40}$-3-({3-(mPeg(30 k)yloxy)propylidene}aminoxy)propyloxy hGH, $N^{\delta 141/40}$-2-(O-(2-(3-(2,3-bis(mPeg(30 k)yloxy)propyloxy)propylamino)-2-oxoethyl)oximino)ethyl hGH, $N^{141/40}$-3-({4-(2,3-bis(mPeg(30 k)yloxy)prop-1-yloxy)propylidene}aminoxy)propyloxy hGH, $N^{\delta 141/40}$-3-({4-{(2,3-bis(mPEG(20 k)yl)prop-1-yloxy)PEGyloxy}butylidene}aminoxy)propyloxy hGH, $N^{\delta 141/40}$-2-((4-(4-((2,3-bis(mPEG(20 k)yl)propyl)PEGyloxy)butyrylamino)butyl)oximino)ethyl hGH, $N^{\delta 141}$-2-(O-(4-{4-(1,3-bis(mPeg(10 k)ylaminocarbonyloxy)prop-2-yloxy)butyryl}-aminobutyl)-oximino)ethyl hGH, $N^{\delta 141}$-2-(O-(4-{4-(mPeg(10 k)yloxy)butyryl}aminobutyl)oximino)ethyl hGH, $N^{\delta 141}$-2-(O-(4-{3-(mPeg(10 k)yloxy)propionyl}aminobutyl)oximino)ethyl hGH, $N^{\delta 141}$-2-(O-(4-{4-(2,3-bis(mPeg(10 k)yloxy)prop-1-yloxy)butyryl}aminobutyl)oximino)ethyl hGH, $N^{\delta 141}$-2-(O-(4-{5-(mPeg(10 k)yloxy-5-oxopentanoyl}aminobutyl)oximino)ethyl hG H, $N^{\delta 141}$-3-({4-(2-(2-(2-(2-(4-(1,3-bis(mPeg(10 k)ylaminocarbonyloxy)prop-2-yloxy)butyrylamino)-ethoxy)ethoxy)ethoxy)butylidene}aminoxy)prop-1-yloxy hGH, $N^{\delta 141}$-3-({4-(1,3-bis(mPeg(10 k)ylaminocarbonyloxy)prop-2-yloxy)butylidene}-aminoxy)propyloxy hGH, $N^{\delta 141}$-3-({4-(mPeg(10 k)yloxy)butylidene}aminoxy)propyloxy hGH, $N^{\delta 141}$-3-({4-(2,3-bis(mPeg(10 k)yloxy)prop-1-yloxy)butylidene}aminoxy)propyloxy hGH, $N^{\delta 141}$-3-({3-(mPeg(10 k)yloxy)propylidene}aminoxy)propyloxy hGH, $N^{\delta 141}$-2-(O-(2-(3-(2,3-bis(mPeg(10 k)yloxy)propyloxy)propylamino)-2-oxoethyl)oximino)ethyl hGH, $N^{\delta 141}$-3-({4-(2,3-bis(mPeg(10 k)yloxy)prop-1-yloxy)propylidene}aminoxy)propyloxy hGH, $N^{\delta 141}$-2-(O-(4-{4-(1,3-bis(mPeg(20 k)ylaminocarbonyloxy)prop-2-yloxy)butyryl}-minobutyl)-oximino)ethyl hGH, $N^{\delta 141}$-2-(O-(4-{3-(mPeg(20 k)yloxy)propionyl}aminobutyl)oximino)ethyl hGH, $N^{\delta 141}$-2-(O-(4-{4-(2,3-bis(mPeg(20 k)yloxy)prop-1-yloxy)butyryl}aminobutyl)oximino)ethyl hGH, $N^{\delta 141}$-2-(O-(4-{5-(mPeg(20 k)yloxy-5-oxopentanoyl}aminobutyl)oximino)ethyl hGH, $N^{\delta 141}$-3-({4-(2-(2-(2-(2-(4-(1,3-bis(mPeg(20 k)ylaminocarbonyloxy)prop-2-yloxy)butyrylamino)-ethoxy)ethoxy)ethoxy)butylidene}aminoxy)prop-1-yloxy hGH, $N^{\delta 141}$-3-({4-(1,3-bis(mPeg(20 k)ylaminocarbonyloxy)prop-2-yloxy)butylidene}-aminoxy)propyloxy hGH, $N^{\delta 141}$-3-({4-(mPeg(20 k)yloxy)butylidene}aminoxy)propyloxy hGH,
$N^{\delta 141}$-3-({4-(2,3-bis(mPeg(20 k)yloxy)prop-1-yloxy)butylidene}aminoxy)propyloxy hGH,
$N^{\delta 141}$-3-({3-(mPeg(20 k)yloxy)propylidene}aminoxy)propyloxy hGH,
$N^{\delta 141}$-2-(O-(2-(3-(2,3-bis(mPeg(20 k)yloxy)propyloxy)propylamino)-2-oxoethyl)oximino)ethyl hGH,
$N^{\delta 141}$-3-({4-(2,3-bis(mPeg(20 k)yloxy)prop-1-yloxy)propylidene}aminoxy)propyloxy hGH,
$N^{\delta 141}$-2-(O-(4-{4-(1,3-bis(mPeg(30 k)ylaminocarbonyloxy)prop-2-yloxy)butyryl}-aminobutyl)-oximino)ethyl hGH,
$N^{\delta 141}$-2-(O-(4-{4-(mPeg(30 k)yloxy)butyryl}aminobutyl)oximino)ethyl hGH,
$N^{\delta 141}$-2-(O-(4-{3-(mPeg(30 k)yloxy)propionyl}aminobutyl)oximino)ethyl hGH,
$N^{\delta 141}$-2-(O-(4-{4-(2,3-bis(mPeg(30 k)yloxy)prop-1-yloxy)butyryl}aminobutyl)oximino)ethyl hGH,
$N^{\delta 141}$-2-(O-(4-{5-(m Peg(30 k)yloxy-5-oxopentanoyl}aminobutyl)oximino)ethyl hGH,
$N^{\delta 141}$-3-({4-(2-(2-(2-(2-(4-(1,3-bis(mPeg(30 k)ylaminocarbonyloxy)prop-2-yloxy)butyrylamino)-ethoxy)ethoxy)ethoxy)ethoxy)butylidene}aminoxy)prop-1-yloxy hGH,
$N^{\delta 141}$-3-({4-(1,3-bis(mPeg(30 k)ylaminocarbonyloxy)prop-2-yloxy)butylidene}-aminoxy)propyloxy hGH,
$N^{\delta 141}$-3-({4-(mPeg(30 k)yloxy)butylidene}aminoxy)propyloxy hGH,
$N^{\delta 141}$-3-({4-(2,3-bis(mPeg(30 k)yloxy)prop-1-yloxy)butylidene}aminoxy)propyloxy hGH,
$N^{\delta 141}$-3-({3-(mPeg(30 k)yloxy)propylidene}aminoxy)propyloxy hGH,
$N^{\delta 141}$-2-(O-(2-(3-(2,3-bis(mPeg(30 k)yloxy)propyloxy)propylamino)-2-oxoethyl)oximino)ethyl hGH,
$N^{\delta 141}$-3-({4-(2,3-bis(mPeg(30 k)yloxy)prop-1-yloxy)propylidene}aminoxy)propyloxy hGH,
$N^{\delta 141}$-3-({4-{(2,3-bis(mPEG(20 k)yloxy)prop-1-yl)PEGyloxy}butylidene}aminoxy)propyloxy hGH,
$N^{\delta 141}$-2-((4-(4-((2,3-bis(mPEG(20 k)yl)propyl)PEGyloxy)butyrylamino)butyl)oximino)ethyl hGH,
$N^{\delta 40}$-2-(O-(4-{4-(1,3-bis(mPeg(10 k)ylaminocarbonyloxy)prop-2-yloxy)butyryl}-aminobutyl)-oximino)ethyl hGH,
$N^{\delta 40}$-2-(O-(4-{4-(mPeg(10 k)yloxy)butyryl}aminobutyl)oximino)ethyl hGH,
$N^{\delta 40}$-2-(O-(4-{3-(mPeg(10 k)yloxy)propionyl}aminobutyl)oximino)ethyl hGH,
$N^{\delta 40}$-2-(O-(4-{4-(2,3-bis(mPeg(10 k)yloxy)prop-1-yloxy)butyryl}aminobutyl)oximino)ethyl hGH,
$N^{\delta 40}$-2-(O-(4-{5-(mPeg(10 k)yloxy-5-oxopentanoyl}aminobutyl)oximino)ethyl hGH,
$N^{\delta 40}$-3-({4-(2-(2-(2-(2-(4-(1,3-bis(mPeg(10 k)ylaminocarbonyloxy)prop-2-yloxy)butyrylamino)-ethoxy)ethoxy)ethoxy)ethoxy)butylidene}aminoxy)prop-1-yloxy hGH,
$N^{\delta 40}$-3-({4-(1,3-bis(mPeg(10 k)ylaminocarbonyloxy)prop-2-yloxy)butylidene}-aminoxy)propyloxy hGH,
$N^{\delta 40}$-3-({4-(mPeg(10 k)yloxy)butylidene}aminoxy)propyloxy hGH,
$N^{\delta 40}$-3-({4-(2,3-bis(mPeg(10 k)yloxy)prop-1-yloxy)butylidene}aminoxy)propyloxy hGH,
$N^{\delta 40}$-3-({3-(mPeg(10 k)yloxy)propylidene}aminoxy)propyloxy hGH,
$N^{\delta 40}$-2-(O-(2-(3-(2,3-bis(mPeg(10 k)yloxy)propyloxy)propylamino)-2-oxoethyl)oximino)ethyl hGH,
$N^{\delta 40}$-3-({4-(2,3-bis(mPeg(10 k)yloxy)prop-1-yloxy)propylidene}aminoxy)propyloxy hGH,
$N^{\delta 40}$-2-(O-(4-{4-(1,3-bis(mPeg(20 k)ylaminocarbonyloxy)prop-2-yloxy)butyryl}-aminobutyl)-oximino)ethyl hGH,
$N^{\delta 40}$-2-(O-(4-{3-(mPeg(20 k)yloxy)propionyl}aminobutyl)oximino)ethyl hGH,
$N^{\delta 40}$-2-(O-(4-{4-(2,3-bis(mPeg(20 k)yloxy)prop-1-yloxy)butyryl}aminobutyl)oximino)ethyl hGH,
$N^{\delta 40}$-(O-(4-{5-(mPeg(20 k)yloxy-5-oxopentanoyl}aminobutyl)oximino)ethyl hGH,
$N^{\delta 40}$-3-({4-(2-(2-(2-(2-(4-(1,3-bis(mPeg(20 k)ylaminocarbonyloxy)prop-2-yloxy)butyrylamino)-ethoxy)ethoxy)ethoxy)ethoxy)butylidene}aminoxy)prop-1-yloxy hGH,
$N^{\delta 40}$-3-({4-(1,3-bis(mPeg(20 k)ylaminocarbonyloxy)prop-2-yloxy)butylidene}-aminoxy)propyloxy hGH,
$N^{\delta 40}$-3-({4-(mPeg(30 k)yloxy)butylidene}aminoxy)propyloxy hGH,
$N^{\delta 40}$-3-({4-(2,3-bis(mPeg(20 k)yloxy)prop-1-yloxy)butylidene}aminoxy)propyloxy hGH,
$N^{\delta 40}$-3-({3-(mPeg(20 k)yloxy)propylidene}aminoxy)propyloxy hGH,
$N^{\delta 40}$-2-(O-(2-(3-(2,3-bis(mPeg(20 k)yloxy)propyloxy)propylamino)-2-oxoethyl)oximino)ethyl hGH,
$N^{\delta 40}$-3-({4-(2,3-bis(mPeg(20 k)yloxy)prop-1-yloxy)propylidene}aminoxy)propyloxy hGH,
$N^{\delta 40}$-2-(O-(4-{4-(1,3-bis(mPeg(30 k)ylaminocarbonyloxy)prop-2-yloxy)butyryl}-aminobutyl)-oximino)ethyl hGH,
$N^{\delta 40}$-2-(O-(4-{4-(mPeg(30 k)yloxy)butyryl}aminobutyl)oximino)ethyl hGH,
$N^{\delta 40}$-2-(O-(4-{3-(mPeg(30 k)yloxy)propionyl}aminobutyl)oximino)ethyl hGH,
$N^{\delta 40}$-2-(O-(4-{4-(2,3-bis(mPeg(30 k)yloxy)prop-1-yloxy)butyryl}aminobutyl)oximino)ethyl hGH,
$N^{\delta 40}$-2-(O-(4-{5-(mPeg(30 k)yloxy-5-oxopentanoyl}aminobutyl)oximino)ethyl hGH,
$N^{\delta 40}$-3-({4-(2-(2-(2-(2-(4-(1,3-bis(mPeg(30 k)ylaminocarbonyloxy)prop-2-yloxy)butyrylamino)-ethoxy)ethoxy)ethoxy)ethoxy)butylidene}aminoxy)prop-1-yloxy hGH,
$N^{\delta 40}$-3-({4-(2,3-bis(mPeg(30 k)ylaminocarbonyloxy)prop-2-yloxy)butylidene}-aminoxy)propyloxy hGH,
$N^{\delta 40}$-3-({4-(mPeg(30 k)yloxy)butylidene}aminoxy)propyloxy hGH,
$N^{\delta 40}$-3-({4-(2,3-bis(mPeg(30 k)yloxy)prop-1-yloxy)butylidene}aminoxy)propyloxy hGH,
$N^{\delta 40}$-3-((3-(mPeg(30 k)yloxy)propylidene)aminoxy)propyloxy hGH,
$N^{\delta 40}$-2-(O-(2-(3-(2,3-bis(mPeg(30 k)yloxy)propyloxy)propylamino)-2-oxoethyl)oximino)ethyl hGH,
$N^{\delta 40}$-3-({4-(2,3-bis(mPeg(30 k)yloxy)prop-1-yloxy)propylidene}aminoxy)propyloxy hGH,
$N^{\delta 40}$-3-((4-{(2,3-bis(mPEG(20 k)yloxy)prop-1-yl)PEGyloxy}butylidene)aminoxy)propyloxy hGH, and
$N^{\delta 40}$-2-((4-(4-((2,3-bis(mPEG(20 k)yl)propyl)PEGyloxy)butyrylamino)butyl)oximino)ethyl hGH.

Embodiment 48: A method of treating a disease benefiting form an increase in the amount of circulating growth hormone, the method comprising the administration of a therapeutically effective amount of a composition according to any of embodiments 1 to 47 to a patient in need thereof.

Embodiment 49: A method according to embodiment 48, wherein said disease is selected from growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; distraction oteogenesis; disorders resulting from hip or discus replacement, meniscus repair, spinal fusions or prosthesis fixation, such as in the knee, hip, shoulder, elbow, wrist or jaw; disorders resulting from fixing of osteosynthesis material, such as nails, screws and plates; non-union or mal-union of fractures; disorders resulting from osteatomia, e.g. from tibia or 1st toe; disorders resulting from graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Crohn's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; and short stature due to glucocorticoid treatment in children.

Embodiment 50: A method according to embodiment 48 or embodiment 49, wherein said disease is selected from growth hormone deficiency (GHD), Turner Syndrome, short for gestational age (SGA), short stature in children born with very low birth weight (VLBW) but SGA, skeletal dysplasia, hypochondroplasia, achondroplasia, idiopathic short stature (ISS), and GHD in adults.

Embodiment 51: Use of a composition according to any of embodiments 1 to 47 in the manufacture of a medicament for the treatment of a disease which will benefit from an increase in the plasma level of growth hormone.

Embodiment 52: Use according to embodiment 51, wherein said disease is selected from growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; distraction oteogenesis; disorders resulting from hip or discus replacement, meniscus repair, spinal fusions or prosthesis fixation, such as in the knee, hip, shoulder, elbow, wrist or jaw; disorders resulting from fixing of osteosynthesis material, such as nails, screws and plates; non-union or mal-union of fractures; disorders resulting from osteatomia, e.g. from tibia or $1^{st}$ toe; disorders resulting from graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Crohn's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; and short stature due to glucucorticoid treatment in children.

Embodiment 53: A method according to embodiment 51 or embodiment 52, wherein said disease is selected from growth hormone deficiency (GHD), Turner Syndrome, short for gestational age (SGA), short stature in children born with very low birth weight (VLBW) but SGA, skeletal dysplasia, hypochondroplasia, achondroplasia, idiopathic short stature (ISS), and GHD in adults.

In one embodiment, the pegylated growth hormone is a pegylated human growth hormone (hGH), which has a amino acid sequence as shown in SEQ ID No. 1.

In one embodiment, the growth hormone is a variant of hGH, wherein a variant is understood to be the compound obtained by substituting one or more amino acid residues in the hGH sequence with another natural or unnatural amino acid; and/or by adding one or more natural or unnatural amino acids to the hGH sequence; and/or by deleting one or more amino acid residue from the hGH sequence, wherein any of these steps may optionally be followed by further derivatization of one or more amino acid residue. In particular, such substitutions are conservative in the sense that one amino acid residue is substituted by another amino acid residue from the same group, i.e. by another amino acid residue with similar properties. Amino acids may conveniently be divided in the following groups based on their properties: Basic amino acids (such as arginine and lysine), acidic amino acids (such as glutamic acid and aspartic acid), polar amino acids (such as glutamine, histidine, cysteine and asparagine), hydrophobic amino acids (such as leucine, isoleucine, proline, methionine and valine), aromatic amino acids (such as phenylalanine, tryptophan, tyrosine) and small amino acids (such as glycine, alanine, serine and threonine).

In one embodiment, the growth hormone has at least 80%, such as at least 85%, such as at least 90%, such as at least 95% identity with a hGH having the amino acid sequence of SEQ ID No. 1. In one embodiment, said identities to hGH is coupled to at least 20%, such as at least 40%, such as at least 60%, such as at least 80% of the growth hormone activity of hGH as determined in assay I herein.

The term "identity" as known in the art, refers to a relationship between the sequences of two or more proteins, as determined by comparing the sequences. In the art, "identity" also means the degree of sequence relatedness between proteins, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related proteins can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Preferred methods to determine identity are designed to give the largest match between the sequences tested. Methods to determine identity are described in publicly available computer programs. Preferred computer program methods to determine identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

For example, using the computer algorithm GAP (Genetics Computer Group, University of Wisconsin, Madison, Wis.), two proteins for which the percent sequence identity is to be determined are aligned for optimal matching of their respective amino acids (the "matched span", as determined by the algorithm). A gap opening penalty (which is calculated as 3.times. the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp.3 (1978) for the PAM 250 comparison matrix; Henikoff et al., Proc. Natl. Acad. Sci. USA 89, 10915-10919 (1992) for the BLOSUM 62 comparison matrix) is also used by the algorithm.

Preferred parameters for a protein sequence comparison include the following:

Algorithm: Needleman et al., J. Mol. Biol. 48, 443-453 (1970); Comparison matrix: BLOSUM 62 from Henikoff et al., Proc. Natl. Acad. Sci. USA 89, 10915-10919 (1992); Gap Penalty: 12, Gap Length Penalty: 4, Threshold of Similarity: 0.

The GAP program is useful with the above parameters. The aforementioned parameters are the default parameters for protein comparisons (along with no penalty for end gaps) using the GAP algorithm.

In one embodiment, the growth hormone is 20 k hGH as described in J. Clin. Endocrin. Metabol. 89, 1562-1571 (2004) and Endocrine J. 47, S49-S52 (2000).

In one embodiment, the growth hormone is hGH in which glutamine 40 has been deleted or substituted with another amino acid, and in particular substituted with asparagine.

In one embodiment, the growth hormone is hGH in which glutamine 141 has been deleted or substituted with another amino acid, and in particular substituted with asparagine.

In one embodiment, growth hormone is hGH which has been extended at the N-terminal with up to 10 amino acids, such as 0, 1, 2, 3, 4, 5, 6, 7, 8, 9, or 10 amino acids. Particular mentioning is made of Ser-X-hGH, wherein X represents a bond or a mono-, di-, tri-, tetra or penta-peptide, and in particular of Ser-hGH.

The variant of hGH are obtainable through protein synthesis using standard protein synthesis techniques as the variants are fairly small. Alternatively, the variants may be obtained by genetic manipulation of a suitable host. A nucleic acid construct encoding the variant is inserted into the host, and upon fermentation of said host, the variant may be isolated from the fermentation broth or as an exclusion body. In any case, nucleic acid and host construction, fermentation and isolation are within the capabilities of a skilled person.

The PEG is typically a mPEG with a molecular weight between 5 and 100 kDa, such as between 10 and 80 k Da, such as 10 20, 30, 40, 60 k Da. The pegylated growth hormone may comprise more than one PEG, typically 2 or 3. Effectively, the corresponds to growth hormone pegylated with a branched PEG. Alternatively, more than one PEG may be conjugated to growth hormone to obtain an increase in the molecular weight of the PEG. In this way, two conjugated PEG with a molecular weight of 20 kDa each will correspond to conjugated PEG with a molecular weight of 40 kDa.

Often, there is a linker between PEG and growth hormone. In fact, the pegylated growth hormone may take the formal structure PEG-linker1-oxime-linker2-growth hormone. linker1 and linker 2 may independently be absent or present. Linker1 and Linker2 are typically used adjust the distance between PEG and growth hormone, or they are the consequence of the manufacture of the functionalised PEG and functionalised growth hormone used in the preparation of pegylated growth hormone. Typically, the linker is a $C_{2-15}$alkylene, wherein one or more methylene are optionally substituted with e.g. O, NH, C(=O), or arylene. The linker may also be small PEG biradicals, i.e. for instance —(CH$_2$—CH$_2$—O)$_{1-15}$.

An oxime bond is formed in the reaction between an carbonyl moiety (i.e. an aldegyde or a ketone) and an oxyamine moiety, and in particular between an aldehyde moiety and an oxyamine moiety

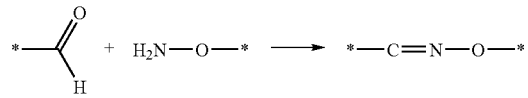

In the above sketched reaction, growth hormone may be the carbonyl or the oxyamine containing moiety. In the same way, the PEG moiety may be the carbonyle or the oxyamine containing moiety. It is, however, understood the PEG moiety and the growth hormone must be complementary in the sense that if the growth hormone is carbonyl, e.g. aldehyde functionalised then the PEG moiety must be oxyamine functionalised, and if the growth hormone is oxyamine functionalised then the PEG moiety must be carbonyl, e.g. aldehyde functionalised.

The natural amino acids do not comprise a carbonyl moiety nor an oxyamine moiety, and it is therefore necessary to introduce these functionalities into growth hormone. In one embodiment, growth hormone is extended at the N-terminal with a Ser-X, wherein X is a defined above. In one embodiment, X represents a bond, and in particular the growth hormone is hGH, i.e. the N-terminal extended growth hormone is Ser-hGH. The alcohol in serine may be oxidised to an aldehyde, e.g. by means of periodate.

Alternatively, transglutaminase may the used to catalyse the reaction between growth hormone and an amine containing nucleophile. The reaction results in a transaminated growth hormone wherein the nucleophile has been introduced at a glutamine in growth hormone. By proper selection of the nucleophile, a carbonyle moiety, i.e. an aldehyde or ketone, an oxyamine, or a group which upon further reaction, e.g. oxidation may be transformed into one of these moieties may be introduced into growth hormone. This is disclosed in for instance WO 05/070468 and PCT application WO2006EP063246.

Alternatively, a growth hormone-derived aldehyde, ketone or oxyamine may be prepared by amide formation of the carboxy-terminal of said growth hormone with an unnatural α-amino acid amide, which contains a ketone, an aldehyde or an oxyamine as side-chain functional group. Alternmatively, said α-amino acid amide may comprise a moiety which upon further reaction may be transformed to one of said functional groups. Such an unnatural α-amino acid amide may be coupled with said protein with the aid of an enzyme, such as a carboxypeptidase. This is disclosed in WO 05/035553.

Alternativly, un-natural amino acids may be incorporated into a protein during fermentation as disclosed in US 2005/0170404.

Aldehyde functionalised PEGs are available e.g. from the companies Shearwater and NOF. Oxyamine functionalised PEGs are not directly available, but they may be obtained by simple chemical manipulations of e.g. succinimidyl functionalised PEG. See examples for details on how to convert a succinimidyl functionalised PEG to an alkoxyamine functionalised PEG.

The pegylated growth hormone is obtained by mixing the functionalised growth hormone with the functionalised PEG, optionally followed by purification, e.g. chromatographic purification.

The concentration of pegylated growth hormone is typically from 0.001 to 200 mg/ml, for instance from 0.001 to 100 mg/ml, such as from 0.01 to 100 mg/ml, for instance from 1 to 100 mg/ml, such as from 5 to 50 mg/ml, for instance from 10 to 50 mg/ml, such as from 30 to 50 mg/ml, for instance about 40 mg/ml. In one embodiment, the concentration of pegylated growth hormone is from 0.01 to 10 mg/ml, such as from 0.1 to 10 mg/ml, for instance from 0.1 to 5 mg/ml.

The list of pegylated growth hormones below represents examples of pegylated growth hormones which advantageously may be formulated in the pharmaceutical compositions of the present invention.

Lys$^\epsilon$(4-((2-(1-(mPEGcarbonyl)piperidin-4-yl)ethoxy) imino)pentanoyl) 192)hGH(1-192) amide, in which mPEG has a molecular weight of 20 kDa;

(S)-2-(hGHylamino)-6-(4-((2-(1-(4-(mPEGyloxy)butanoyl) piperidin-4-yl)ethoxy)imino)pentanoylamino)hexanoic amide, in which mPEG has a molecular weight of 10 kDa;

N$^{\epsilon 141}$-[2-(4-(4-(mPEG(20 k)ylbutanoyl)-amino-butyloxy-imino)-ethyl]hGH, N$^{\epsilon 41}$-[2-(1-(hexadecanoyl)piperidin-4-yl)ethyloxyimino)-ethyl]hGH, N$^{\epsilon 41}$ (2-(4-(4-(1,3-bis(mPEG(20 k)ylaminocarbonyloxy) prop-2-yloxy)butyrylamino)butyloxy-imino)ethyl]hGH, N$^{\epsilon 141}$ (2-(4-(2,6-bis(mPEG(20 k)yloxycarbonylamino)hexanoylamino)butyloxyimino)ethyl]hGH, N$^{\epsilon 141}$ (2-(4-(4-(mPEG(30 k)yloxy)butyrylamino)butyloxy-imino)ethyl]hGH, N$^{\epsilon 141}$ (2-(4-(4-(mPEG(20 k)yloxy)butyrylamino)butyloxy-imino)ethyl]hGH, and NE$^{141}$ (2-(4-(3-(mPEG(30k)yloxy) propanoylamino)butyloxyimino)ethyl]hGH;

[MeO—(CH$_2$CH$_2$O)$_{400-500}$—CH$_2$CH$_2$—NH—C(=O)—O—CH$_2$]$_2$CH—O—(CH$_2$)$_3$—C(=O)—NH—(CH$_2$)$_4$—O—N=CH—C(=O)-GH,

[MeO—(CH$_2$CH$_2$O)$_{600-750}$](CH$_2$)$_3$—C(=O)NH—(CH$_2$)$_4$—CH[MeO—(CH$_2$CH$_2$O)$_{600-750}$—(CH$_2$)$_3$C(=O)NH]—C(=O)NH—(CH$_2$)$_4$-Q-N=CH—C(=O)-GH,

MeO—(CH$_2$CH$_2$O)$_{400-500}$—CH$_2$CH$_2$CH$_2$—C(=O)—NH—(CH$_2$)$_4$—O—N=CH—C(=O)-GH,

MeO—(CH$_2$CH$_2$O)$_{600-700}$—CH$_2$CH$_2$CH$_2$—C(=O)—NH—(CH$_2$)$_4$—O—N=CH—C(=O)-GH,

MeO—(CH$_2$CH$_2$O)$_{850-950}$—CH$_2$CH$_2$CH$_2$—C(=O)—NH—(CH$_2$)$_4$—O—N=CH—C(=O)-GH,

[MeO—(CH$_2$CH$_2$O)$_{400-500}$]—C(=O)NH—(CH$_2$)$_4$—CH[MeO—(CH$_2$CH$_2$O)$_{400-500}$—C(=O)NH]—C(=O)NH—(CH$_2$)$_4$—O—N=CH—C(=O)-GH,

[MeO—(CH$_2$CH$_2$O)$_{600-700}$]—C(=O)NH—(CH$_2$)$_4$—CH[MeO—(CH$_2$CH$_2$O)$_{600-700}$—C(=O)NH]—C(=O)NH—(CH$_2$)$_4$—O—N=CH—C(=O)-GH,

MeO—(CH$_2$CH$_2$O)$_{400-500}$—CH$_2$CH$_2$CH$_2$—C(=O)—NH—(CH$_2$)$_4$—O—N=CH—CH$_2$—O—(CH$_2$)$_4$-GH,

MeO—(CH$_2$CH$_2$O)$_{600-700}$—CH$_2$CH$_2$CH$_2$—C(=O)—NH—(CH$_2$)$_4$—O—N=CH—CH$_2$—O—(CH$_2$)$_4$-GH,

MeO—(CH$_2$CH$_2$O)$_{850-950}$—CH$_2$CH$_2$CH$_2$—C(=O)—NH—(CH$_2$)$_4$—O—N=CH—CH$_2$—O—(CH$_2$)$_4$-GH,

[MeO—(CH$_2$CH$_2$O)$_{400-500}$]—C(=O)NH—(CH$_2$)$_4$—CH[MeO—(CH$_2$CH$_2$O)$_{400-500}$—C(=O)NH]—C(=O)NH—(CH$_2$)$_4$—O—N=CH—CH$_2$—O—(CH$_2$)$_4$-GH,

MeO—(CH$_2$CH$_2$O)$_{400-500}$—CH$_2$CH$_2$CH$_2$—C(=O)—NH—(CH$_2$)$_4$—O—N=CH—CH$_2$—O—(CH$_2$)$_5$-GH,

MeO—(CH$_2$CH$_2$O)$_{600-700}$—CH$_2$CH$_2$CH$_2$—C(=O)—NH—(CH$_2$)$_4$—O—N=CH—CH$_2$—O—(CH$_2$)$_5$-GH,

MeO—(CH$_2$CH$_2$O)$_{850-950}$—CH$_2$CH$_2$CH$_2$—C(=O)—NH—(CH$_2$)$_4$—O—N=CH—CH$_2$—O—(CH$_2$)$_5$-GH,

[MeO—(CH$_2$CH$_2$O)$_{400-500}$]—C(=O)NH—(CH$_2$)$_4$—CH[MeO—(CH$_2$CH$_2$O)$_{400-500}$—C(=O)NH]—C(=O)NH—(CH$_2$)$_4$—O—N=CH—CH$_2$—O—(CH$_2$)$_5$-GH,

MeO—(CH$_2$CH$_2$O)$_{400-500}$—CH$_2$CH$_2$CH$_2$—C(=O)—NH—(CH$_2$)$_4$—O—N=CH—CH$_2$—O—(CH$_2$)$_6$-GH,

MeO—(CH$_2$CH$_2$O)$_{600-700}$—CH$_2$CH$_2$CH$_2$—C(=O)—NH—(CH$_2$)$_4$—O—N=CH—CH$_2$—O—(CH$_2$)$_6$-GH,

MeO—(CH$_2$CH$_2$O)$_{850-950}$—CH$_2$CH$_2$CH$_2$—C(=O)—NH—(CH$_2$)$_4$—O—N=CH—CH$_2$—O—(CH$_2$)$_6$-GH,

[MeO—(CH$_2$CH$_2$O)$_{400-500}$]—C(=O)NH—(CH$_2$)$_4$—CH[MeO—(CH$_2$CH$_2$O)$_{400-500}$—C(=O)NH]—C(=O)NH—(CH$_2$)$_4$—O—N=CH—CH$_2$—O—(CH$_2$)$_6$-GH,

MeO—(CH$_2$CH$_2$O)$_{400-500}$—CH$_2$CH$_2$CH$_2$—C(=O)—NH—(CH$_2$)$_4$—O—N=CH—CH$_2$—O-(1,4-C$_6$H$_4$)CH$_2$-GH,

MeO—(CH$_2$CH$_2$O)$_{600-700}$—CH$_2$CH$_2$CH$_2$—C(=O)—NH—(CH$_2$)$_4$—O—N=CH—CH$_2$—O-(1,4-C$_6$H$_4$)CH$_2$-GH,

MeO—(CH$_2$CH$_2$O)$_{850-950}$—CH$_2$CH$_2$CH$_2$—C(=O)—NH—(CH$_2$)$_4$—O—N=CH—CH$_2$—O-(1,4-C$_6$H$_4$)CH$_2$-GH,

[MeO—(CH$_2$CH$_2$O)$_{400-500}$]—C(=O)NH—(CH$_2$)$_4$—CH[MeO—(CH$_2$CH$_2$O)$_{400-500}$—C(=O)NH]—C(=O)NH—(CH$_2$)$_4$—O—N=CH—CH$_2$—O-(1,4-C$_6$H$_4$)CH$_2$-GH,

MeO—(CH$_2$CH$_2$O)$_{400-500}$—CH$_2$CH$_2$CH$_2$—C(=O)—NH—(CH$_2$)$_4$—O—N=CH—CH$_2$—O-(1,3-C$_6$H$_4$)CH$_2$-GH,

MeO—(CH$_2$CH$_2$O)$_{600-700}$—CH$_2$CH$_2$CH$_2$—C(=O)—NH—(CH$_2$)$_4$—O—N=CH—CH$_2$—O-(1,3-C$_6$H$_4$)CH$_2$-GH,

MeO—(CH$_2$CH$_2$O)$_{850-950}$—CH$_2$CH$_2$CH$_2$—C(=O)—NH—(CH$_2$)$_4$—O—N=CH—CH$_2$—O-(1,3-C$_6$H$_4$)CH$_2$-GH,

[MeO—(CH$_2$CH$_2$O)$_{400-500}$]—C(=O)NH—(CH$_2$)$_4$—CH[MeO—(CH$_2$CH$_2$O)$_{400-500}$—C(=O)NH]—C(=O)NH—(CH$_2$)$_4$—O—N=CH—CH$_2$—O-(1,3-C$_6$H$_4$)CH$_2$-GH,

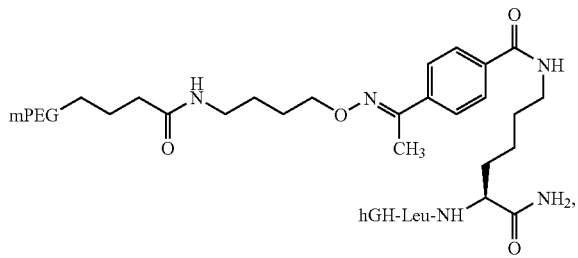

in which mPEG has a molecular weight around 5 kDa, 10 kDa, 15 kDa, 20 kDa, 30 kDa, 40 kDa or 60 kDa;

$N^{\delta 141/40}$-2-(O-(4-{4-(mPeg(10 k)yloxy)butyryl}aminobutyl)oximino)ethyl hGH, $N^{\delta 141/40}$-2-(O-(4-{3-(mPeg(10 k)yloxy)propionyl}aminobutyl)oximino)ethyl hGH, $N^{\delta 141/40}$-2-(O-(4-{4-(2,3-bis(mPeg(10 k)yloxy)prop-1-yloxy)butyryl}aminobutyl)oximino)ethyl hGH, $N^{\delta 141/40}$-2-(O-(4-{5-(mPeg(10 k)yloxy-5-oxopentanoyl}aminobutyl)oximino)ethyl hGH, $N^{\delta 141/40}$-3-({4-(2-(2-(2-(2-(4-(1,3-bis(mPeg(10 k)ylaminocarbonyloxy)prop-2-yloxy)butyrylamino)ethoxy)ethoxy)ethoxy)butylidene}aminoxy)prop-1-yloxy hGH, $N^{\delta 141/40}$-3-({4-(1,3-bis(mPeg(10 k)ylaminocarbonyloxy)prop-2-yloxy)butylidene}aminoxy)propyloxy hGH, $N^{\delta 141/40}$-3-({4-(mPeg(10 k)yloxy)butylidene}aminoxy)propyloxy hGH, $N^{\delta 141/40}$-3-({4-(2,3-bis(mPeg(10 k)yloxy)prop-1-yloxy)butylidene}aminoxy)propyloxy hGH, $N^{\delta 141/40}$-3-({3-(mPeg(10 k)yloxy)propylidene}aminoxy)propyloxy hGH, $N^{\delta 141/40}$-2-(O-(2-(3-(2,3-bis(mPeg(10 k)yloxy)propyloxy)propylamino)-2-oxoethyl)oximino)ethyl hGH, $N^{\delta 141/40}$-3-({4-(2,3-bis(mPeg(10 k)yloxy)prop-1-yloxy)propylidene}aminoxy)propyloxy hGH, $N^{141/40}$-2-(O-(4-{4-(1,3-bis(mPeg(20 k)ylaminocarbonyloxy)prop-2-yloxy)butyryl}aminobutyl)-oximino)ethyl hGH, $N^{\delta 141/40}$-2-(O-(4-{3-(mPeg(20 k)yloxy)propionyl}aminobutyl)oximino)ethyl hGH, $N^{\delta 141/40}$-2-(O-(4-{4-(2,3-bis(mPeg(20 k)yloxy)prop-1-yloxy)butyryl}aminobutyl)oximino)ethyl hGH, $N^{\delta 141/40}$-2-(O-(4-{5-(mPeg(20 k)yloxy-5-oxopentanoyl}aminobutyl)oximino)ethyl hGH, $N^{\delta 141/40}$-3-({4-(2-(2-(2-(2-(4-(1,3-bis(mPeg(20 k)ylaminocarbonyloxy)prop-2-yloxy)butyrylamino)ethoxy)ethoxy)ethoxy)butylidene}aminoxy)prop-1-yloxy hGH, $N^{\delta 141/40}$-3-({4-(1,3-bis(mPeg(20 k)ylaminocarbonyloxy)prop-2-yloxy)butylidene}-aminoxy)propyloxy hGH, $N^{\delta 141/40-3}$-({4-(mPeg(20 k)yloxy)butylidene}aminoxy)propyloxy hGH, $N^{\delta 141/40}$-3-({4-(2,3-bis(mPeg(20 k)yloxy)prop-1-yloxy)butylidene}aminoxy)propyloxy hGH, $N^{\delta 141/40}$-3-({3-(mPeg(20 k)yloxy)propylidene}aminoxy)propyloxy hGH, $N^{\delta 141/40}$-2-(O-(2-(3-(2,3-bis(mPeg(20 k)yloxy)propyloxy)propylamino)-2-oxoethyl)oximino)ethyl hGH, $N^{\delta 141/40}$-3-({4-(2,3-bis(mPeg(20 k)yloxy)prop-1-yloxy)propylidene}aminoxy)propyloxy hGH, $N^{\delta 141/40}$-2-(O-(4-{4-(1,3-bis(mPeg(30 k)ylaminocarbonyloxy)prop-2-yloxy)butyryl}aminobutyl)oximino)ethyl hGH, $N^{\delta 141/40}$-2-(O-(4-{4-(mPeg(30 k)yloxy)butyryl}aminobutyl)oximino)ethyl hGH, $N^{\delta 141/40}$-2-(O-(4-{3-(mPeg(30 k)yloxy)propionyl}aminobutyl)oximino)ethyl hGH, $N^{\delta 141/40}$-2-(O-(4-{4-(2,3-bis(mPeg(30 k)yloxy)prop-1-yloxy)butyryl}aminobutyl)oximino)ethyl hGH, $N^{\delta 141/40}$-2-(O-(4-{5-(mPeg(30 k)yloxy-5-oxopentanoyl}aminobutyl)oximino)ethyl hGH, $N^{\delta 141/40}$-3-({4-(2-(2-(2-(2-(4-(1,3-bis(mPeg(30 k)ylaminocarbonyloxy)prop-2-yloxy)butyrylamino)ethoxy)ethoxy)ethoxy)butylidene}aminoxy)prop-1-yloxy hGH, $N^{141/40}$-3-({4-(1,3-bis(mPeg(30 k)ylaminocarbonyloxy)prop-2-yloxy)butylidene}-aminoxy)propyloxy hGH, $N^{\delta 141/40}$-3-({4-(mPeg(30 k)yloxy)butylidene}aminoxy)propyloxy hGH, $N^{\delta 141/40}$-3-({4-(2,3-bis(mPeg(30 k)yloxy)prop-1-yloxy)butylidene}aminoxy)propyloxy hGH, $N^{\delta 141/40}$-3-({3-(mPeg(30 k)yloxy)propylidene}aminoxy)propyloxy hGH, $N^{\delta 141/40}$-2-(O-(2-(3-(2,3-bis(mPeg(30 k)yloxy)propyloxy)propylamino)-2-oxoethyl)oximino)ethyl hGH, $N^{\delta 141/40}$-3-({4-(2,3-bis(mPeg(30 k)yloxy)prop-1-yloxy)propylidene}aminoxy)propyloxy hGH, $N^{\delta 141/40}$-3-({4-{(2,3-bis(mPEG(20 k)yl)prop-1-yloxy)PEGyloxy}butylidene}aminoxy)propyloxy hGH, $N^{\delta 141/40}$-2-((4-(4-((2,3-bis(mPEG(20 k)yl)propyl)PEGyloxy)butyrylamino)butyl)oximino)ethyl hGH, $N^{\delta 141}$-2-(O-(4-(4-(1,3-bis(mPeg(10 k)ylaminocarbonyloxy)prop-2-yloxy)butyryl)-aminobutyl)oximino)ethyl hGH, $N^{\delta 141}$-2-(O-(4-(4-(mPeg(10 k)yloxy)butyryl)aminobutyl)oximino)ethyl hGH, $N^{\delta 141}$-2-(O-(4-{3-(mPeg(10 k)yloxy)propionyl}aminobutyl)oximino)ethyl hGH, $N^{\delta 141}$-2-(O-(4-{4-(2,3-bis(mPeg(10 k)yloxy)prop-1-yloxy)butyryl}aminobutyl)oximino)ethyl hGH, $N^{\delta 141}$-2-(O-(4-{5-(mPeg(10 k)yloxy-5-oxopentanoyl}aminobutyl)oximino)ethyl hGH, $N^{\delta 141}$-3-({4-(2-(2-(2-(2-(4-(1,3-bis(mPeg(10 k)ylaminocarbonyloxy)prop-2-yloxy)butyrylamino)ethoxy)ethoxy)ethoxy)butylidene}aminoxy)prop-1-yloxy hGH, $N^{\delta 141}$-3-({4-(1,3-bis(mPeg(10 k)ylaminocarbonyloxy)prop-2-yloxy)butylidene}-aminoxy)propyloxy hGH, $N^{\delta 141}$-3-({4-(mPeg(10 k)yloxy)butylidene}aminoxy)propyloxy hGH, $N^{\delta 141}$-3-({4-(2,3-bis(mPeg(10 k)yloxy)prop-1-yloxy)butylidene}aminoxy)propyloxy hGH, $N^{\delta 141}$-3-({3-(mPeg(10 k)yloxy)propylidene}aminoxy)propyloxy hGH, $N^{\delta 141}$-2-(O-(2-(3-(2,3-bis(mPeg(10 k)yloxy)propyloxy)propylamino)-2-oxoethyl)oximino)ethyl hGH, $N^{\delta 141}$-3-({4-(2,3-bis(mPeg(10 k)yloxy)prop-1-yloxy)propylidene}aminoxy)propyloxy hGH, $N^{\delta 141}$-2-(O-(4-{4-(1,3-bis(mPeg(20 k)ylaminocarbonyloxy)prop-2-yloxy)butyryl}-minobutyl)oximino)ethyl hGH, $N^{\delta 141}$-2-(O-(4-{3-(mPeg(20 k)yloxy)propionyl}aminobutyl)oximino)ethyl hGH, $N^{\delta 141}$-2-(O-(4-{4-(2,3-bis(mPeg(20 k)yloxy)prop-1-yloxy)butyryl}aminobutyl)oximino)ethyl hGH, $N^{\delta 141}$-2-(O-(4-{5-(mPeg(20 k)yloxy-5-oxopentanoyl}aminobutyl)oximino)ethyl hGH, $N^{\delta 141}$-3-({4-(2-(2-(2-(2-(4-(1,3-bis(mPeg(20 k)ylaminocarbonyloxy)prop-2-yloxy)butyrylamino)ethoxy)ethoxy)ethoxy)butylidene}aminoxy)prop-1-yloxy hGH, $N^{\delta 141}$-3-({4-(1,3-bis(mPeg(20 k)ylaminocarbonyloxy)prop-2-yloxy)butylidene}aminoxy)propyloxy hGH, $N^{\delta141}$-3-({4-(mPeg(20 k)yloxy)butylidene}aminoxy)propyloxy hGH, $N^{\delta141}$-3-({4-(2,3-bis(mPeg(20 k)yloxy)prop-1-yloxy)butylidene}aminoxy)propyloxy hGH, $N^{\delta141}$-3-({3-(mPeg(20 k)yloxy)propylidene}aminoxy)propyloxy hGH, $N^{\delta141}$-2-(O-(2-(3-(2,3-bis(mPeg(20 k)yloxy)propyloxy)propylamino)-2-oxoethyl)oximino)ethyl hGH, $N^{\delta141}$-3-({4-(2,3-bis(mPeg(20 k)yloxy)prop-1-yloxy)propylidene}aminoxy)propyloxy hGH, $N^{\delta141}$-2-(O-(4-{4-(1,3-bis(mPeg(30 k)ylaminocarbonyloxy)prop-2-yloxy)butyryl}-aminobutyl)oximino)ethyl hGH, $N^{\delta141}$-2-(O-(4-{4-(mPeg(30 k)yloxy)butyryl}aminobutyl)oximino)ethyl hGH, $N^{\delta141}$-2-(O-(4-{3-(mPeg(30 k)yloxy)propionyl}aminobutyl)oximino)ethyl hGH, $N^{\delta141}$-2-(O-(4-{4-(2,3-bis(mPeg(30 k)yloxy)prop-1-yloxy)butyryl}aminobutyl)oximino)ethyl hGH, $N^{\delta141}$-2-(O-(4-{5-(mPeg(30 k)yloxy-5-oxopentanoyl}aminobutyl)oximino)ethyl hGH, $N^{\delta141}$-3-({4-(2-(2-(2-(2-(4-(1,3-bis(mPeg(30 k)ylaminocarbonyloxy)prop-2-yloxy)butyrylamino)ethoxy)ethoxy)ethoxy)ethoxy)butylidene}aminoxy)prop-1-yloxy hGH, $N^{\delta141}$-3-({4-(1,3-bis(mPeg(30 k)ylaminocarbonyloxy)prop-2-yloxy)butylidene}aminoxy)propyloxy hGH, $N^{\delta141}$-3-({4-(mPeg(30 k)yloxy)butylidene}aminoxy)propyloxy hGH, $N^{\delta141}$-3-({4-(2,3-bis(mPeg(30 k)yloxy)prop-1-yloxy)butylidene}aminoxy)propyloxy hGH, $N^{\delta141}$-3-({3-(mPeg(30 k)yloxy)propylidene}aminoxy)propyloxy hGH, $N^{\delta141}$-2-(O-(2-(3-(2,3-bis(mPeg(30 k)yloxy)propyloxy)propylamino)-2-oxoethyl)oximino)ethyl hGH, $N^{\delta141}$-3-({4-(2,3-bis(mPeg(30 k)yloxy)prop-1-yloxy)propylidene}aminoxy)propyloxy hGH, $N^{\delta141}$-3-({4-((2,3-bis(mPEG(20 k)yloxy)prop-1-yl)PEGyloxy)butylidene}aminoxy)propyloxy hGH, $N^{\delta141}$-2-((4-(4-((2,3-bis(m PEG(20 k)yl)propyl)PEGyloxy)butyrylamino)butyl)oximino)ethyl hGH, $N^{\delta40}$-2-(O-(4-{4-(1,3-bis(mPeg(10 k)ylaminocarbonyloxy)prop-2-yloxy)butyryl}-aminobutyl)oximino)ethyl hGH, $N^{\delta40}$-2-(O-(4-{4-(mPeg(10 k)yloxy)butyryl}aminobutyl)oximino)ethyl hGH, $N^{\delta40}$-2-(O-(4-{3-(mPeg(10 k)yloxy)propionyl}aminobutyl)oximino)ethyl hGH, $N^{\delta40}$-2-(O-(4-{4-(2,3-bis(mPeg(10 k)yloxy)prop-1-yloxy)butyryl}aminobutyl)oximino)ethyl hGH, $N^{\delta40}$-2-(O-(4-{5-(mPeg(110 k)yloxy-5-oxopentanoyl}aminobutyl)oximino)ethyl hGH, $N^{\delta40}$-3-({4-(2-(2-(2-(2-(4-(1,3-bis(mPeg(10 k)ylaminocarbonyloxy)prop-2-yloxy)butyrylamino)ethoxy)ethoxy)ethoxy)ethoxy)butylidene}aminoxy)prop-1-yloxy hGH, $N^{\delta40}$-3-({4-(1,3-bis(mPeg(10 k)ylaminocarbonyloxy)prop-2-yloxy)butylidene}-aminoxy)propyloxy hGH, $N^{\delta40}$-3-({4-(mPeg(10 k)yloxy)butylidene}aminoxy)propyloxy hGH, $N^{\delta40}$-3-({4-(2,3-bis(mPeg(10 k)yloxy)prop-1-yloxy)butylidene}aminoxy)propyloxy hGH, $N^{\delta40}$-3-({3-(mPeg(10 k)yloxy)propylidene}aminoxy)propyloxy hGH, $N^{\delta40}$-2-(O-(2-(3-(2,3-bis(mPeg(10 k)yloxy)propyloxy)propylamino)-2-oxoethyl)oximino)ethyl hGH, $N^{\delta40}$-3-({4-(2,3-bis(mPeg(10 k)yloxy)prop-1-yloxy)propylidene}aminoxy)propyloxy hGH, $N^{\delta40}$-2-(O-(4-{4-(1,3-bis(mPeg(20 k)ylaminocarbonyloxy)prop-2-yloxy)butyryl}aminobutyl)oximino)ethyl hGH, $N^{\delta40}$-2-(O-(4-{3-(mPeg(20 k)yloxy)propionyl}aminobutyl)oximino)ethyl hGH, $N^{\delta40}$-2-(O-(4-{4-(2,3-bis(mPeg(20 k)yloxy)prop-1-yloxy)butyryl}aminobutyl)oximino)ethyl hGH, $N^{\delta40}$-2-(O-(4-{5-(mPeg(20 k)yloxy-5-oxopentanoyl}aminobutyl)oximino)ethyl hGH, $N^{\delta40}$-3-({4-(2-(2-(2-(2-(4-(1,3-bis(mPeg(20 k)ylaminocarbonyloxy)prop-2-yloxy)butyrylamino)ethoxy)ethoxy)ethoxy)ethoxy)butylidene}aminoxy)prop-1-yloxy hGH, $N^{\delta40}$-3-({4-(1,3-bis(mPeg(20 k)ylaminocarbonyloxy)prop-2-yloxy)butylidene}-aminoxy)propyloxy hGH, $N^{\delta40}$)-3-({4-(mPeg(20 k)yloxy)butylidene}aminoxy)propyloxy hGH, $N^{\delta40}$-3-({4-(2,3-bis(mPeg(20 k)yloxy)prop-1-yloxy)butylidene}aminoxy)propyloxy hGH, $N^{\delta40}$-3-({3-(mPeg(20 k)yloxy)propylidene}aminoxy)propyloxy hGH, $N^{\delta40}$-2-(O-(2-(3-(2,3-bis(mPeg(20 k)yloxy)propyloxy)propylamino)-2-oxoethyl)oximino)ethyl hGH, $N^{\delta40}$-3-({4-(2,3-bis(mPeg(20 k)yloxy)prop-1-yloxy)propylidene}aminoxy)propyloxy hGH, $N^{\delta40}$-2-(O-(4-{4-(1,3-bis(mPeg(30 k)ylaminocarbonyloxy)prop-2-yloxy)butyryl}aminobutyl)oximino)ethyl hGH, $N^{\delta40}$-2-(O-(4-{4-(mPeg(30 k)yloxy)butyryl}aminobutyl)oximino)ethyl hGH, $N^{\delta40}$-2-(O-(4-{3-(mPeg(30 k)yloxy)propionyl}aminobutyl)oximino)ethyl hGH, $N^{\delta40}$-2-(O-(4-{4-(2,3-bis(mPeg(30 k)yloxy)prop-1-yloxy)butyryl}aminobutyl)oximino)ethyl hGH, $N^{\delta40}$-2-(O-(4-{5-(mPeg(30 k)yloxy-5-oxopentanoyl}aminobutyl)oximino)ethyl hGH, $N^{\delta40}$-3-({4-(2-(2-(2-(2-(4-(1,3-bis(mPeg(30 k)ylaminocarbonyloxy)prop-2-yloxy)butyrylamino)ethoxy)ethoxy)ethoxy)ethoxy)butylidene}aminoxy)prop-1-yloxy hGH, $N^{\delta40}$-3-({4-(1,3-bis(mPeg(30 k)ylaminocarbonyloxy)prop-2-yloxy)butylidene}aminoxy)propyloxy hGH, $N^{\delta40}$-3-({4-(mPeg(30 k)yloxy)butylidene}aminoxy)propyloxy hGH, $N^{\delta40}$-3-({4-(2,3-bis(mPeg(30 k)yloxy)prop-1-yloxy)butylidene}aminoxy)propyloxy hGH, Nδ40-3-({3-(mPeg(30 k)yloxy)propylidene}aminoxy)propyloxy hGH, $N^{\delta40}$-2-(O-(2-(3-(2,3-bis(mPeg(30 k)yloxy)propyloxy)propylamino)-2-oxoethyl)oximino)ethyl hGH, $N^{\delta40}$-3-({4-(2,3-bis(mPeg(30 k)yloxy)prop-1-yloxy)propylidene}aminoxy)propyloxy hGH, $N^{\delta40}$-3-({4-{(2,3-bis(mPEG(20 k)yloxy)prop-1-yl)PEGyloxy}butylidene}aminoxy)propyloxy hGH; and $N^{\delta40}$-2-((4-(4-((2,3-bis(mPEG(20 k)yl)propyl)PEGyloxy)butyrylamino)butyl)oximino)ethyl hGH.

The pharmaceutical compositions of the present invention have pH of 7 or below. In one embodiment pH is from 1 to 7, such as from 2 to 6, such as from 3 to 5, In one embodiment, pH is from 4 to 7, such as from 5 to 7, such as from 6 to 7. In one embodiment, the pH is from 4.5 to 7, such as from 5.5 to 7, such as from 6.5 to 7. In one embodiment, pH is from 5.5 to 6.5, such as around 6.1.

The pharmaceutical compositions of the present invention do not comprise carbonate in any substantial amount. "Substantial amount" is taken to indicate an amount which influences the stability of the pegylated growth hormone. In one embodiment, carbonate is present in an amount less than $10^{-3}$ M, such as below $10^{-4}$ M, such as below $10^{-5}$ M. It should be noted that carbonate exists in an acid-base equilibrium

and that "carbonate" is taken to be the sum of all the above carbonate forms.

The pharmaceutically compositions of the present invention typically comprises further excipients known in the art, such as buffers, preservatives, isotonic agents, chelating agents, stabilizers, amino acids or amino acid derivatives, surfactants, wetting agents, emulsifiers, antioxidants, bulking agents, metal ions, oleaginous vehicles, proteins (e.g., human serum albumin, gelatine or proteins) and a zwitterions. The use of these excipients is well known to the person skilled in the art and described in e.g. Remington: The Science and Practice of Pharmacy, $20^{th}$ edition, 2000.

In one embodiment, the amino acid or amino acid derivative used as excipient is histidine; Y-His, wherein Y represents an amino acid residue; poly-His; or des-amino-His. Particular mentioning is made of histidine.

In one embodiment, histidine is present in an amount from 0.001 to 10 mg pr mg of pegylated growth hormone, such as from 0.1 to 10 mg per mg of pegylated growth hormone, for instance from 0.1 to 5 mg per mg of pegylated growth hormone, such as from 0.1 to 1 mg per mg of pegylated growth hormone, for instance from 0.3 to 0.7 mg per mg of pegylated growth hormone.

In one embodiment, histidine is present in an amount from 0.002 to 0.35 mg per mg of pegylated growth hormone, such as from 0.0025 to 0.17 mg per mg of pegylated growth hormone, for instance from 0.003 to 0.035 mg per mg of pegylated growth hormone, such as from 0.005 to 0.025 mg per mg of pegylated growth hormone, for instance from 0.01 to 0.02 mg per mg of pegylated growth hormone.

In one embodiment, histidine will be present in an amount from 0.001 to 10 mg pr mg of growth hormone, such as from 0.1 to 10 mg per mg of growth hormone, for instance from 0.1 to 5 mg per mg of growth hormone, such as from 0.1 to 1 mg per mg of growth hormone, for instance from 0.3 to 0.7 mg per mg of growth hormone.

In one embodiment, histidine will be present in an amount from 0.001 to 10 mg pr mg of growth hormone, such as from 0.005 to 1 mg per mg of growth hormone, for instance from 0.01 to 1 mg per mg of growth hormone, such as from 0.02 to 0.05 mg per mg of growth hormone, wherein the weight of the growth hormone is calculated without taking the presence of the PEG moiety into account.

In one embodiment, the pharmaceutical composition comprises histidine in an amount from 0.05 to 100 mg/ml, such as from 0.05 to 50 mg/ml, for instance from 0.05 to 10 mg/ml, such as from 0.05 to 1 mg/ml, for instance from 0.1 to 0.5 mg/ml, such as from 0.2 to 0.4 mg/ml, for instance about 0.34 mg/ml.

In one embodiment, the amino acid or amino acid derivative used as excipient is glycine. Typically glycine is present in an amount from 1 to 20 mg/ml, for instance from 2 to 20 mg/ml or from 1 to 10 mg/ml, such as from 2 to 10 mg/ml, such as from 3 to 7 mg/ml or from 2 to 7 mg/ml, such as around 2.2 mg/ml or as around 4.5 mg/ml.

In one embodiment, the surfactant used as excipient is a non-ionic surfactant, such as e.g. polysorbate or poloxamer. Particular examples include polysorbate 20, poloxamer 188 or poloxamer 407. Particular mentioning is made of poloxamer 188. The non-ionic surfactant is typically present in an amount from 1 to 10 mg/ml, such as from 1 to 5 mg/ml, for instance from 1 to 4 mg/ml or from 2 to 4 mg/ml, such as around 1.5 mg/ml or around 3 mg/ml.

In one embodiment, the pharmaceutical compositions of the present invention comprise a sugar alcohol, such as mannitol, xylitol, threitol, sorbitol or glycerol. In one embodiment, the sugar alcohol is mannitol. Mannitol may be present in an amount from 5 to 100 mg/ml, such as from 5 to 80 mg/ml, for instance from 10 to 80 mg/ml, such as from 10 to 60 mg/ml, for instance from 30 to 60 mg/ml or from 15 to 50 mg/ml, such as from 30 to 50 mg/ml, for instance around 20 mg/ml or around 40 mg/ml. In one embodiment, mannitol is present in an amount from 5 to 50 mg/ml, such as from 10 to 50 mg/ml or from 5 to 30 mg/ml, for instance from 10 to 30 mg/ml, such as from 20 to 25 mg/ml (for instance around 22 mg/ml) or from 10 to 15 mg/ml (for instance around 11 mg/ml).

In one embodiment, the pharmaceutical compositions of the present invention comprise a phosphate buffer to stabilise pH. Typically, a mixture of a mono-hydrogen phosphate salt and a di-hydrogen phosphate salt is used, e.g. with a subsequent adjustment of pH. Many phosphate salts may be used, such as sodium or potassium salts. In one embodiment, the total amount of phosphate is from 2 to 50 mM, such as from 5 to 50 mM (for instance from 5 to 20 mM) or from 2 to 20 mM, such as around 5 mM (for instance 4.5 mM) or around 10 mM.

In one embodiment, the composition of the present invention comprises a phophate buffer at a concentration from 5 to 50 mM, such as 10 mM at a pH from 5 to 7.

In one embodiment, the composition of the present invention comprises an acetate buffer at a concentration from 5 to 50 mM, such as 10 mM at a pH from 5 to 7.

In one embodiment, the composition of the present invention comprises a citrate buffer at a concentration from 5 to 50 mM, such as 10 mM at a pH from 5 to 7.

In one embodiment, the pharmaceutical compositions of the present invention comprise preservatives, such as m-cresol, phenol or benzylalcohol, and in particular phenol. The preservatives may be present in an amount from 1 to 10 mg/ml, such as from 1 to 5 mg/ml, for instance around 2.5 mg/ml or around 5 mg/ml.

In one embodiment, the pharmaceutical compositions of the present invention comprise

| | | |
|---|---|---|
| A) | pegylated growth hormone | |
| | Histidine: | 0.3 to 0.7 mg/mg |
| | Poloxamer 188: | 1-5 mg/ml |
| | Mannitol: | 30-50 mg/ml |
| | pH: | 5.5-6.5; |
| or | | |
| B) | pegylated growth hormone | |
| | Histidine: | 0.54 mg/mg |
| | Poloxamer 188: | 3 mg/ml |
| | Mannitol: | 40 mg/ml |
| | pH: | 6.1; |
| or | | |
| C) | pegylated growth hormone | |
| | Glycine: | 2-10 mg/ml |
| | Mannitol: | 10-30 mg/ml |
| | $NaH_2PO_4 + Na_2HPO_4$: | 5-20 mM |
| | pH: | 5-7; |
| or | | |
| D) | pegylated growth hormone | |
| | Glycine: | 4.4 mg/ml |
| | Mannitol: | 22 mg/ml |
| | $NaH_2PO_4 + Na_2HPO_4$: | 9.2 mM |
| | pH: | 5-7 |
| or | | |
| E) | pegylated growth hormone | |
| | Histidine: | 0.002 to 0.34 mg/mg pegylated growth hormone |
| | Poloxamer 188: | 1-5 mg/ml |
| | Mannitol: | 30-50 mg/ml |
| | pH: | 5.5-6.5; |

| | | |
|---|---|---|
| or | | |
| F) | pegylated growth hormone | |
| | Histidine: | 0.0085 mg/mg pegylated growth hormone |
| | Poloxamer 188: | 3 mg/ml |
| | Mannitol: | 40 mg/ml |
| | pH: | 6.1; |
| or | | |
| G) | pegylated growth hormone | |
| | Glycine: | 2-10 mg/ml |
| | Mannitol: | 10-30 mg/ml |
| | $NaH_2PO_4 + Na_2HPO_4$: | 4-20 mM |
| | pH: | 5-7 |
| or | | |
| H) | pegylated growth hormone | |
| | Glycine: | 2.2 mg/ml |
| | Mannitol: | 11 mg/ml |
| | $NaH_2PO_4 + Na_2HPO_4$: | 4.5 mM |
| | pH: | 5-7. |

Particular mentioning is made of any of the above listed pegylated growth homones formulated in any of compositions A), B), C) or D), and in particular B) or D).

In one embodiment, the above mentioned pegylated growth hormones are formulated in a composition comprising acetate, citrate or phosphate buffer at a buffer concentration from 5 to 50 mM, such as 10 mM and a pH 5-7.

The compositions of the present invention are useful in the treatment of diseases or states which will benefit from an increase in the amount of circulating growth hormone. In particular, the invention provides a method for the treatment of growth hormone deficiency (GHD); Turner Syndrome; Prader-Willi syndrome (PWS); Noonan syndrome; Down syndrome; chronic renal disease, juvenile rheumatoid arthritis; cystic fibrosis, HIV-infection in children receiving HAART treatment (HIV/HALS children); short children born short for gestational age (SGA); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of food; patients after tendon or ligament surgery in e.g. hand, knee, or shoulder; patients having or going through distraction oteogenesis; patients after hip or discus replacement, meniscus repair, spinal fusions or prosthesis fixation, such as in the knee, hip, shoulder, elbow, wrist or jaw; patients into which osteosynthesis material, such as nails, screws and plates, have been fixed; patients with non-union or mal-union of fractures; patients after osteatomia, e.g. from tibia or $1^{st}$ toe; patients after graft implantation; articular cartilage degeneration in knee caused by trauma or arthritis; osteoporosis in patients with Turner syndrome; osteoporosis in men; adult patients in chronic dialysis (APCD); malnutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Crohn's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; or short stature due to glucucorticoid treatment in children, the method comprising administering to a patient in need thereof a therapeutically effective amount of a pharmaceutical composition of the present invention.

In one aspect, the invention provides a method for the acceleration of the healing of muscle tissue, nervous tissue or wounds; the acceleration or improvement of blood flow to damaged tissue; or the decrease of infection rate in damaged tissue, the method comprising administration to a patient in need thereof an effective amount of a therapeutically effective amount of a pharmaceutical composition of the present invention.

A "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on e.g. the severity of the disease or injury as well as the weight, sex, age and general state of the subject. It will be understood that determining an appropriate dosage may be achieved using routine experimentation, by constructing a matrix of values and testing different points in the matrix, which is all within the ordinary skills of a trained physician or veterinary.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The patient to be treated is preferably a mammal, in particular a human being, but it may also include animals, such as dogs, cats, cows, sheep and pigs. Nonetheless, it should be recognized that therapeutic regimens and prophylactic (preventative) regimens represent separate aspects of the invention.

In one embodiment, the invention relates to the use of compositions of the present invention in the manufacture of diseases benefiting from an increase in the growth hormone plasma level, such as the disease mentioned above.

A typical parenteral dose is in the range of $10^{-9}$ mg/kg to about 100 mg/kg body weight growth hormone per administration. Typical administration doses are from about 0.0000001 to about 10 mg/kg body weight per administration. The exact dose will depend on e.g. indication, medicament, frequency and mode of administration, the sex, age and general condition of the subject to be treated, the nature and the severity of the disease or condition to be treated, the desired effect of the treatment and other factors evident to the person skilled in the art.

Typical dosing frequencies are twice daily, once daily, bi-daily, twice weekly, once weekly or with even longer dosing intervals. Due to the prolonged half-lifes of the pegylated growth hormones, a dosing regime with long dosing intervals, such as twice weekly, once weekly or with even longer dosing intervals is a particular embodiment of the invention.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

EXAMPLES

Example 1

Oxyamine Functionalised PEG a) 2-(4-(tert-Butoxycarbonylaminoxy)butyl)isoindole-1,3-dione

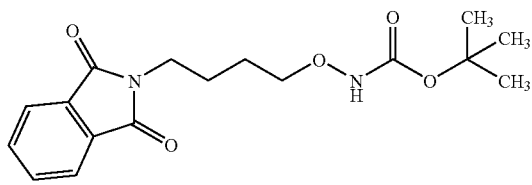

To a mixture of commercially available N-(4-bromobutyl) phthalimide (2.82 g, 10 mmol) and N-Boc-hydroxylamine (2.08 g, 15.6 mmol) was added acetonitrile (2 ml) and successively 1,8-diazabicyclo[5.4.0]undec-7-ene (2.25 ml, 15 mmol). The reaction mixture was stirred at room temperature for 30 min and then at 50° C. for 2 days. It was diluted with a mixture of water (30 ml) and 1 N hydrochloric acid (20 ml). It was extracted with ethyl acetate (2×100 ml). The organic phase was washed with brine (50 ml) and was dried over magnesium sulphate. The crude product was purified by chromatography on silica (60 g), using a gradient of heptane/ethyl acetate 1:0 to 0:1 as eluent to give 2.08 g of 2-(4-(tert-butoxycarbonylaminoxy)butyl)isoindole-1,3-dione.

b) N-(4-aminobutoxy)carbamic acid tert-butyl ester

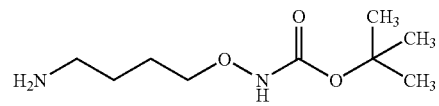

Hydrazine hydrate (1.0 ml, 20 mmol) was added to a solution of 2-(4-(tert-butoxycarbonylaminoxy)butyl)isoindole-1,3-dione (2.08 g, 6.22 mmol) in ethanol (8.0 ml). The reaction mixture was stirred at 80° C. for 65 h. The solvent was removed in vacuo. The residue was dissolved in toluene (10 ml) and the solvent was removed in vacuo. The residue was suspended in 1 N hydrochloric acid (10 ml). The precipitation was removed by filtration and was washed with water (2 ml). The filtrate and the wash-liquids were combined and made basic with potassium carbonate. The solution was extracted with dichloromethane (4×20 ml). The organic layer was dried over magnesium sulphate. The solvent was removed in vacuo to give 0.39 g of N-(4-aminobutoxy)carbamic acid tert-butyl ester. Potassium carbonate (3 g) was added to the aqueous phase, which was extracted with dichloromethane (3×20 ml). These combined organic layers were dried over magnesium sulphate. The solvent was removed in vacuo to give another 0.39 g of N-(4-aminobutoxy)carbamic acid tert-butyl ester.

c) N-(4-(4-(mPEG20000-yl)butanolyamino)butoxy) carbamic acid tert-butyl ester

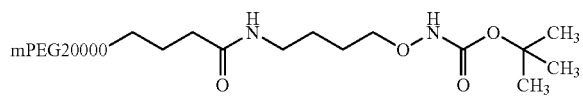

The commercially available N-hydroxysuccinimide ester of mPEG2000-ylbutanoic acid (Nektar "mPEG-SBA", # 2M450P01, 3 g, 0.15 mmol) was dissolved in dichloromethane (25 ml). N-(4-Aminobutoxy)carbamic acid tert-butyl ester (0.12 g, 0.59 mmol) was added. The reaction mixture was shaken at room temperature. Diethyl ether was added until a precipitation was obtained. The precipitation was isolated by filtration. The material was dried in vacuo to yield 2.39 g of N-(4-(4-(mPEG20000-yl)butanolyamino)butoxy)carbamic acid tert-butyl ester.

d) N-(4-Aminoxybutyl)-4-(mPEG20000-yl)butanolyamide

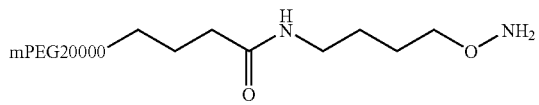

Trifluoroacetic acid (20 ml) was added to a solution of N-(4-(4-(mPEG20000-yl)-butanolyamino)butoxy)carbamic acid tert-butyl ester (2.39 g, 0.12 mmol) in dichloromethane (20 ml). The reaction mixture was shaken for 30 min. Diethyl ether (100 ml) was added. The formed precipitation was isolated by filtration. It was washed with diethyl ether (2×100 ml) and dried in vacuo to give 1.96 g of N-(4-aminoxybutyl)-4-(mPEG20000-yl)butanolyamide Example 2

Aldehyde Functionalised hGH a) Ser-hGH

The Ser-hGH analogue expression plasmid was created on the basis of pNNC13 (Zbasic2mt-D4K-hGH), which expresses the wild type hGH in fusion with Zbasic domain (MVDNKFNKERRRARREIRHLPNLNREQR-RAPIRSLRDDPSQSANLLAEAKKLNRAQAPKY RGGSDDDDKSFPTIPLSRLFDNAML-RAHRLHQLAFDTYQEFEEAYIPKEQKYSFLQNPQTSL CFSESIPTPSNREETQQKSNLELLRIS-LLLIQSWLEPVQFLRSVFANSLVYGASDSNVYDLLK DLEEGIQTLMGRLEDGSPRTGQIFKQ-TYSKFDTNSHNDDALLKNYGLLYCFRKD-MDKVETFL RIVQCRSVEGSCGF, SEQ ID No. 2). Additional Ser was inserted in front of Phe, the first amino acid of mature hGH, by QuikChange® XL Site-Directed Mutagenesis Kit from Stratagene with a pair of primes:

```
5' end: pNNC13 Ser-F:
5'-GGATCAGACGACGACGACAAAagcTTCCCAACCATTCCCTTATCC-3' and 3'end: pNNC13 Ser-R:
5'-GGATAAGGGAATGGTTGGGAAgctTTTGTCGTCGTCGTCTGATCC-3'.
```

E. coli BL21 (DE3) was transformed by pET111a-Zbasic2mt-D4K-Ser-hGH. Single colony was inoculated into 100 ml LB media with 100 µg/ml Amp and grew at 37° C. When OD600 reached 0.6, the cell culture temperature was reduced to 30° C., and the cells were induced with 1 mM IPTG for 4 hours at 30° C. The bacteria cells were harvested by centrifugation at 3000 g for 15 minutes (Eppendorf centrifuge 5810R). The cell pellet was re-suspended in cell lysis buffer (25 mM $Na_2HPO_4$ 25 mM $NaH_2PO_4$ pH 7, 5 mM EDTA, 0.1% Triton X-100), and the cells were disrupted by cell disruption at 30 kpsi (Constant Cell Disruption Systems). The lysate was clarified by centrifugation at 1000 g for 30 minutes. The supernatant was saved and used for purification, while the pellet was discarded.

Zbasic2mt-D4K-Ser-hGH was purified on SP-Sepharose using a step gradient elution (buffer A: 25 mM $Na_2HPO_4$ 25 mM $NaH_2PO_4$ pH 7; buffer B: 25 mM $Na_2HPO_4$ 25 mM $NaH_2PO_4$ pH 7, 1 M NaCl). The protein was subsequently cleaved using Enteropeptidase for the release of Ser-hGH. Ser-hGH was further purified on a Butyl Sepharose 4FF column to separate the product from the Zbasic2mt-D4K domain and Enteropeptidase (buffer A: 100 mM Hepes pH 7.5; buffer B: 100 mM Hepes pH 7.5, 2 M NaCl, a linear gradient was used). The final product of Ser-hGH was buffer exchanged and lyophilized from 50 mM $NH_4HCO_3$, pH 7.8.

b) Oxidation of Ser-hGH

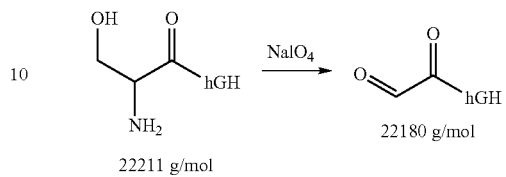

The following solutions were prepared:
Buffer: 25 µl (188 µmol) triethanolamine (Mwt: 149.21, d: 1.12) in water (10 ml)
Methionine (Mwt: 149.21): 20 mg (134 µmol) in water (1.0 ml)
$NaIO_4$ (Mwt: 213.89): 5 mg (23.3 µmol) in water (1.0 ml)
AcOH (Mwt: 60, d: 1): 17 µl (283 µmol) in water (1.0 ml)
Ser-hGH (Mwt: 22211; approx 1 mg, 45 nmol) was dissolved in the buffer (110 µl). To this solution was added the methionine solution (10 µl, approx 30 eq) followed by the $NaIO_4$ solution (10 µl, approx 5 eq). The clear solution was kept at room temperature for 15 min. A solution of the hydroxylamine (10 µl; approx 10 eq) was added and the resulting, slightly turbid mixture was kept at room temperature for 15 min.

Then the solution of AcOH (10 µl, approx 60 eq) was added, and after approx 1 min water (0.5 ml) and the above triethanolamine buffer (0.5 ml) were added. Analysis by HPLC and Maldi indicated at least 80% conversion to the desired oxime.

Example 3

Aldehyde Functionalised hGH a) Trans-amination of hGH to give $N^{\epsilon141}$-(2-hydroxy-3-amino-propyl) hGH hGH (200 mg) was dissolved in phosphate buffer (50 mM, pH 8.0, 14 ml).

This solution was mixed with a solution of 1,3-Diamino-propan-2-ol (378 mg) dissolved in phosphate buffer (50 mM, 1 ml, pH 8.0, pH adjusted to 8.0 with dilute hydrochloric acid after dissolution of 1,3-Diamino-propan-2-ol).

Finally a solution of transglutaminase (18 mg ~40 U) dissolved in phosphate buffer (50 mM, pH 8.0, 1 ml) was added and the volume was adjusted to 10 ml by addition of phosphate buffer (50 mM, pH 8) giving a concentration of 1,3-diamino-propan-2-ol at 0.2 M. The combined mixture was incubated for 4 hours at 37° C.

The temperature was lowered to room temperature and N-ethyl-maleimide was added to a final concentration of 1 mM.

After further 1 hour the mixture was diluted with 10 volumes of tris buffer (50 mM, pH 8.5)

b) Ion exchange chromatography of $N^{\epsilon141}$-(2-hydroxy-3-amino-propyl) hGH The solution resulting from a) was applied to a MonoQ 10/100 GL column (Amersham Biosciences cat. No. 17-5167-01) prequilibrated with buffer A (50 mM tris, pH 8.5). It was then eluted at a flow of 2 ml/min with a gradient of 3% to 6% of buffer B (50 mM tris, 2 M NaCl, pH 8.5) in buffer A over 40 min. Fractions were collected based on UV absorption at 280 nm and Maldi-T of analysis was performed on selected fractions. The fractions corresponding to the largest peak giving the expected mw according to Maldi-T of mass spectrometry were pooled.

c) Characterization of $N^{\delta 141}$-(2-hydroxy-3-amino-propyl) hGH

Peptide mapping of the pool collected in b) showed that the Asp-N fragment AA 130-146 displayed a mass increase of 73 amu corresponding to the addition of the amino alcohol in the side chain of a Glutamine residue. This was the only peptide, that had changed retention time in the HPLC map when compared to that of native hGH. This fragment contains two Glutamine residues. The peptide was subjected to Edman sequencing and Gln-137 was found at the expected yield, whereas Gln-141 displayed a blank Edman cycle. It was concluded, that derivatization had taken place selectively at Gln-141.

d) Oxidation of $N^{\delta 141}$-(2-hydroxy-3-amino-propyl) hGH to Give $N^{\delta 141}$-(2-oxo-etyl) hGH The buffer of the pooled fractions from b) containing 48.7 mg was exchanged four times to a 15 mM triethanolamine pH 8.5 (adjusted with 1 N hydrochloric acid) buffer using an Amicon Ultra-15 ultrafiltration device (Millipore). Finally the solution was concentrated to 2 ml To this was added 2 mll of a 100 mM methionine solution in 15 mM triethanolamine buffer at pH 8.5. Finally 0.4 ml of a 25 mM sodiumperiodate in water was added, and the mixture was incubated for 30 min at room temperature. Then it was cooled on ice and 1.6 ml ice cold N,N-dimethylformamide was added.

Example 4

Oximation of $N^{\delta 141}$-(2-oxo-etyl) hGH with N-(4-Aminooxy-butyl)-4-mPEGyl-butyramide to Give $N^{\epsilon 141}$-[2-(4-(4-(mPEGyl)butanoyl)-amino-butyloxyimino)-ethyl]hGH wherein mPEGyl is polydisperse and has a molecular weight of approximately 20 kDa 380 mg N-(4-Aminooxy-butyl)-4-mPEGyl-butyramide was dissolved in 4 ml water and pH adjusted to 6.0 with 1 N hydrochloric acid. The mixture resulting from example 3 was then added slowly under gentle mixing and the reaction was allowed to proceed at room temperature for 72 h.
Ion Exchange Chromatography The solution resulting from a) was applied to a MonoQ 10/100 GL column (Amersham Biosciences cat. No. 17-5167-01) pre-equilibrated with buffer A (50 mM tris, pH 8.5). It was then eluted at a flow of 0.5 ml/min with a gradient of 0% to 7% of buffer B (50 mM tris, 2 M NaCl, pH 8.5) in buffer A over 1120 min. Fractions were collected based on UV absorption at 280 nm and Maldi-T of analysis was performed on selected fractions. The fractions corresponding to the largest peak giving the expected mw according to Maldi-T of mass spectrometry were pooled. Maldi-T of analysis gave a broad peak centered around 43130 Da in agreement with the polydisperse nature of mPEG. SDS page showed a single band with an apparent molecular weight of 60 kDa. The band stained both with silver and with barium iodide, confirming that it was a PEG derivatized protein. These analytical results confirmed that the isolated product compound was a mono pegylated derivative of hGH.

Example 5

PEG Linker Stability

The stability of [1-(PEG-30000)—O—$CH_2CH_2CH_2CONH$—$(CH_2)_4$—O—N=CH—CO]-hGH was tested in the following compositions at 1 mg/ml as a function of pH. The compound was prepared by oxidising the serine alcohol in Ser-hGH to aldehyde followed by a coupling to PEG-30K-hydroxylamine.

The buffers are made in double concentration and mixed with an equal amount of growth hormone solution.
Buffer—Double Concentration

| Histidine buffer | Carbonate buffer | Phosphate buffer |
|---|---|---|
| 0.68 mg/ml Histidin | 20 mg/ml Glycin | Glycine 4.4 mg/ml, |
| 3 mg/ml Poloxamer 188 | 2.5 mg/ml NaHCO3 | Mannitol 22 mg/ml, |
| 40 mg/ml Mannitol | 2 mg/ml Mannitol | $NaH_2PO_4$ 0.55 mg/ml |
| pH 6.1 | pH 8.2 | $Na_2HPO_4$ 0.65 mg/ml |
| | | pH 7.3. |

Final Buffer Concentration:

| Histidine buffer | Carbonate buffer | Phosphate buffer |
|---|---|---|
| 0.34 mg/ml Histidin | 10 mg/ml Glycin | Glycine 2.2 mg/ml, |
| 1.5 mg/ml Poloxamer 188 | 1.2 mg/ml NaHCO3 | Mannitol 11 mg/ml, |
| 20 mg/ml Mannitol | 1 mg/ml Mannitol | $NaH_2PO_4$ 0.27 mg/ml |
| pH 6.1 | pH 8.2 | $Na_2HPO_4$ 0.32 mg/ml |
| | | pH 7.3. |

The compositions were incubated for two weeks at 40° C., and samples were withdrawn for SEC-HLPC analysis after 1 and 2 weeks. The results indicated as % purity are shown in Table 1.

TABLE 1

| | 1 week | | 2 weeks | |
|---|---|---|---|---|
| Buffer | pH 6.1 | pH 7.3 | pH 6.1 | pH 7.3 |
| Histidine | 96 | 96 | | |
| Carbonate | 74 | 74 | 63 | 63 |
| Phophate | 95 | 95 | | |

Example 6

Chemical Stability

The stability of the same pegylated compound as in example 5 was tested in the following buffers at 1.25 mg/ml as a function of pH. The sodium phosphate, sodium carbonate and histidine buffers were 10 mM. The samples were incubated for 1 week at 40° C. and samples were withdrawn for SEC-HPLC analysis. The major break down product is a 22 kDa species which corresponds to the size of depegylated growth hormone. Table 2 shows the percentage of the 22 kDa species formed.

TABLE 2

| Buffer | pH 5.5 | 6.0 | 6.5 | 7.0 | 7.5 | 8.0 |
|---|---|---|---|---|---|---|
| Phosphate | 1 | 1 | 1 | 1 | 5 | 9 |
| Phosphate buffer as in Example 5 |  |  |  |  | 4 |  |
| Histidine | 1 | 1 | 1 |  |  |  |
| Histidine buffer as in Example 5 | 1 | 1 | 2 |  |  |  |
| Carbonate |  |  |  | 46 | 46 | 48 |

Example 7

The stability of 1-[(mPEG(20 k)NHC(=O)OCH$_2$)$_2$CH—O—CH$_2$CH$_2$CH$_2$CONH—(CH$_2$)$_4$—O—N=CH—CO]-hGH was studied in various buffers as a function of pH at a concentration of 1.3 mg/ml. The compound was prepared by oxidising the serine alcohol in Ser-hGH to aldehyde followed by a coupling to a branched PEG-40K-hydroxylamine. The sodium phosphate, sodium carbonate, sodium citrate, histidine, Tris and glycine buffers were 10 mM. The samples were incubated for 4 weeks at 40° C. and samples were withdrawn for SEC-HPLC analysis. Table 3 shows the purity (%) of the pegylated growth hormone after 4 weeks at 40° C.

FIG. 1 shows the amount of depegylated growth hormone formed as a function of pH in different buffers.

TABLE 3

| | pH 3 | 3.5 | 4 | 4.5 | 5 | 5.5 | 6 | 6.5 | 7 | 7.5 | 8 | 8.5 | 9 | 9.5 | 10 |
|---|---|---|---|---|---|---|---|---|---|---|---|---|---|---|---|
| Citrate | 73.7 | 85.6 | 84.7 | 83.2 | 96.7 | 97.3 | 96.3 |  |  |  |  |  |  |  |  |
| Acetate |  | 35.3 | 39.9 | 72.1 | 96.4 | 97.4 |  |  |  |  |  |  |  |  |  |
| Phosphate |  |  |  |  |  | 99.2 | 95.7 | 96.3 | 94.8 | 91.2 | 86.7 |  |  |  |  |
| Histidine |  |  |  |  |  | 78.2 | 81.6 | 93 |  |  |  |  |  |  |  |
| Tris |  |  |  |  |  |  |  |  | 95.2 | 91 | 89.9 | 89 | 84.8 |  |  |
| Glycine |  |  |  |  |  |  |  |  |  |  |  |  | 79.5 | 63 | 27.2 |

Pharmacological Methods

Assay (I) BAF-3 GHR Assay to Determine Growth Hormone Activity

The BAF-3 cells (a murine pro-B lymphoid cell line derived from the bone marrow) was originally IL-3 dependent for growth and survival. II-3 activates JAK-2 and STAT which are the same mediators GH is activating upon stimulation. After transfection of the human growth hormone receptor the cell line was turn into a growth hormone-dependent cell line. This clone can be used to evaluate the effect of different growth hormone samples on the survival of the BAF-3 GHR.

The BAF-3 GHR cells are grown in starvation medium (culture medium without growth hormoen) for 24 hours at 37° C., 5% CO$_2$.

The cells are washed and re-suspended in starvation medium and seeded in plates. 10 μl of growth hormone compound or human growth hormone in different concentrations or control is added to the cells, and the plates are incubated for 68 hours at 37° C., 5% CO.

AlamarBlue® is added to each well and the cells are then incubated for another 4 hours. The AlamarBlue® is a redox indicator, and is reduced by reactions innate to cellular metabolism and, therefore, provides an indirect measure of viable cell number.

Finally, the metabolic activity of the cells is measure in a fluorescence plate reader. The absorbance in the samples is expressed in % of cells not stimulated with growth hormone compound or control and from the concentration-response curves the activity (amount of a compound that stimulates the cells with 50%) can be calculated.

The invention claimed is:

1. A pharmaceutical composition comprising a pegylated growth hormone and at least one pharmaceutically acceptable excipient, wherein said pegylated growth hormone comprises a growth hormone and a PEG, wherein said growth hormone and said PEG is connected via an oxime bond, and optionally via a linker, wherein said composition does not comprise any substantial amount of carbonate and said composition has a pH from 5 to 7, wherein the PEG moiety is attached to the growth hormone at a serine in the N-terminal of said growth hormone and wherein the composition comprises:

| | |
|---|---|
| Histidine: | 0.002 to 0.34 mg per mg of pegylated growth hormone |
| Poloxamer 188: | 1 to 4 mg/ml |
| Mannitol: | 10 to 30 mg/ml |
| Phenol: | 1 to 5 mg/ml |
| pegylated growth hormone: | 1 to 200 mg/ml |
| pH: | 5-7. |

2. The composition according to claim 1 comprising

| | |
|---|---|
| Histidine: | 0.0085 mg per mg of pegylated growth hormone |
| Poloxamer 188: | 1.5 mg/ml |
| Mannitol: | 20 mg/ml |
| Phenol: | 5 mg/ml |
| pegylated growth hormone: | 1 to 200 mg/ml |
| pH: | 6.1. |

3. A pharmaceutical composition comprising a pegylated growth hormone and at least one pharmaceutically acceptable excipient, wherein said pegylated growth hormone comprises a growth hormone and a PEG, wherein said growth hormone and said PEG is connected via an oxime bond, and optionally via a linker, wherein said composition does not comprise any substantial amount of carbonate and said composition has a pH from 5 to 7, wherein the PEG moiety is attached to the growth hormone at a serine in the N-terminal of said growth hormone and wherein the composition comprises:

| | |
|---|---|
| Glycin: | 2 to 7 mg/ml |
| Mannitol: | 10 to 30 mg/ml |
| Total $PO_4^{3-}$: | 2 to 20 mM |
| Phenol: | 1 to 5 mg/ml |
| pegylated growth hormone: | 1 to 200 mg/ml |
| pH: | 5-7 |

4. The composition according to claim 3 comprising

| | |
|---|---|
| Glycin: | 2.2 mg/ml |
| Mannitol: | 11 mg/ml |
| Total $PO_4^{3-}$: | 4.5 mM |
| Phenol: | 5 mg/ml |
| pegylated growth hormone: | 1 to 200 mg/ml |
| pH: | 5-7 |

* * * * *

UNITED STATES PATENT AND TRADEMARK OFFICE
CERTIFICATE OF CORRECTION

| | | |
|---|---|---|
| PATENT NO. | : 8,293,708 B2 | Page 1 of 1 |
| APPLICATION NO. | : 12/063278 | |
| DATED | : October 23, 2012 | |
| INVENTOR(S) | : Mats Reslow | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 643 days.

Signed and Sealed this
Thirteenth Day of May, 2014

Michelle K. Lee
*Deputy Director of the United States Patent and Trademark Office*

SEQUENCE LISTING

```
<160> NUMBER OF SEQ ID NOS: 2

<210> SEQ ID NO 1
<211> LENGTH: 191
<212> TYPE: PRT
<213> ORGANISM: Homo sapiens

<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
```

```
                    85                  90                  95
Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
            130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                    165                 170                 175

Leu Arg Ile Val Gln Cys Arg Ser Val Glu Gly Ser Cys Gly Phe
                    180                 185                 190

<210> SEQ ID NO 2
<211> LENGTH: 261
<212> TYPE: PRT
<213> ORGANISM: Homo sapiens

<400> SEQUENCE: 2

Met Val Asp Asn Lys Phe Asn Lys Glu Arg Arg Ala Arg Arg Glu
1               5                   10                  15

Ile Arg His Leu Pro Asn Leu Asn Arg Glu Gln Arg Ala Pro Ile
                    20                  25                  30

Arg Ser Leu Arg Asp Asp Pro Ser Gln Ser Ala Asn Leu Leu Ala Glu
            35                  40                  45

Ala Lys Lys Leu Asn Arg Ala Gln Ala Pro Lys Tyr Arg Gly Gly Ser
50                  55                  60

Asp Asp Asp Asp Lys Ser Phe Pro Thr Ile Pro Leu Ser Arg Leu Phe
65                  70                  75                  80

Asp Asn Ala Met Leu Arg Ala His Arg Leu His Gln Leu Ala Phe Asp
                    85                  90                  95

Thr Tyr Gln Glu Phe Glu Glu Ala Tyr Ile Pro Lys Glu Gln Lys Tyr
            100                 105                 110

Ser Phe Leu Gln Asn Pro Gln Thr Ser Leu Cys Phe Ser Glu Ser Ile
            115                 120                 125

Pro Thr Pro Ser Asn Arg Glu Glu Thr Gln Gln Lys Ser Asn Leu Glu
            130                 135                 140

Leu Leu Arg Ile Ser Leu Leu Leu Ile Gln Ser Trp Leu Glu Pro Val
145                 150                 155                 160

Gln Phe Leu Arg Ser Val Phe Ala Asn Ser Leu Val Tyr Gly Ala Ser
                    165                 170                 175

Asp Ser Asn Val Tyr Asp Leu Leu Lys Asp Leu Glu Glu Gly Ile Gln
            180                 185                 190

Thr Leu Met Gly Arg Leu Glu Asp Gly Ser Pro Arg Thr Gly Gln Ile
            195                 200                 205

Phe Lys Gln Thr Tyr Ser Lys Phe Asp Thr Asn Ser His Asn Asp Asp
            210                 215                 220

Ala Leu Leu Lys Asn Tyr Gly Leu Leu Tyr Cys Phe Arg Lys Asp Met
225                 230                 235                 240

Asp Lys Val Glu Thr Phe Leu Arg Ile Val Gln Cys Arg Ser Val Glu
                    245                 250                 255

Gly Ser Cys Gly Phe
            260
```